United States Patent [19]
Seale et al.

[11] Patent Number: 6,131,459
[45] Date of Patent: Oct. 17, 2000

[54] LINEARIZED ULTRASOUND BEAM ALIGNMENT SERVO

[75] Inventors: Joseph B. Seale, Gorham, Me.; Gary E. Bergstrom, Moreland Hills, Ohio

[73] Assignee: P. D. Coop, Inc., Gorham, Me.

[21] Appl. No.: 09/299,287

[22] Filed: Apr. 26, 1999

[51] Int. Cl.[7] .................................................. G01N 29/26
[52] U.S. Cl. ........................ 73/633; 73/620; 73/621; 310/90.5; 600/437; 600/443; 600/453
[58] Field of Search ..................... 310/905, 334; 73/602, 620, 625, 626, 633, 641, 642, 643, 621, 634; 600/425, 437, 440, 441, 444, 445, 453, 455, 456, 457, 459, 407

[56] References Cited

U.S. PATENT DOCUMENTS

| | | | |
|---|---|---|---|
| 4,092,867 | 6/1978 | Matzuk | 73/609 |
| 4,874,998 | 10/1989 | Hollis, Jr. | 318/568.21 |
| 5,160,877 | 11/1992 | Fujiwara et al. | 318/568.21 |
| 5,313,950 | 5/1994 | Ishikawa et al. | 128/662.06 |
| 5,558,091 | 9/1996 | Acker et al. | 128/653.1 |
| 5,635,784 | 6/1997 | Seale | 310/90.5 |
| 5,818,137 | 10/1998 | Nichols et al. | 310/90.5 |
| 5,844,140 | 12/1998 | Seale | |
| 5,936,370 | 8/1999 | Fukao et al. | 318/652 |

*Primary Examiner*—Hezron Williams
*Assistant Examiner*—Rose M. Miller
*Attorney, Agent, or Firm*—Pierce Atwood; Chris A. Caseiro

[57] ABSTRACT

A levitated rotor, neutrally buoyed in ultrasound transmission fluid, moves to position and aim an ultrasound transducer in up to five servo-controlled coordinates of position and tilt rotation. Stator drive/sense windings drive the rotor via a rotor magnet and sense coordinates via inductive interactions with a rotor coil. For five-axis control, one set of stator windings controls two-axis lateral translation while a second set controls axial translation plus two-axis tilt rotation. The windings produce a comparatively linear relationship between the five rotor geometric coordinates and the electromagnetic couplings that drive and sense these coordinates. To produce this linearity seamlessly over a wide coordinate range coming close to the windings, each set of windings is divided into overlapping subsets. A two-way drive/sense matrix mapping translates between up to five control coordinates and more than five winding circuits.

20 Claims, 9 Drawing Sheets

FIG. 1
(prior art)
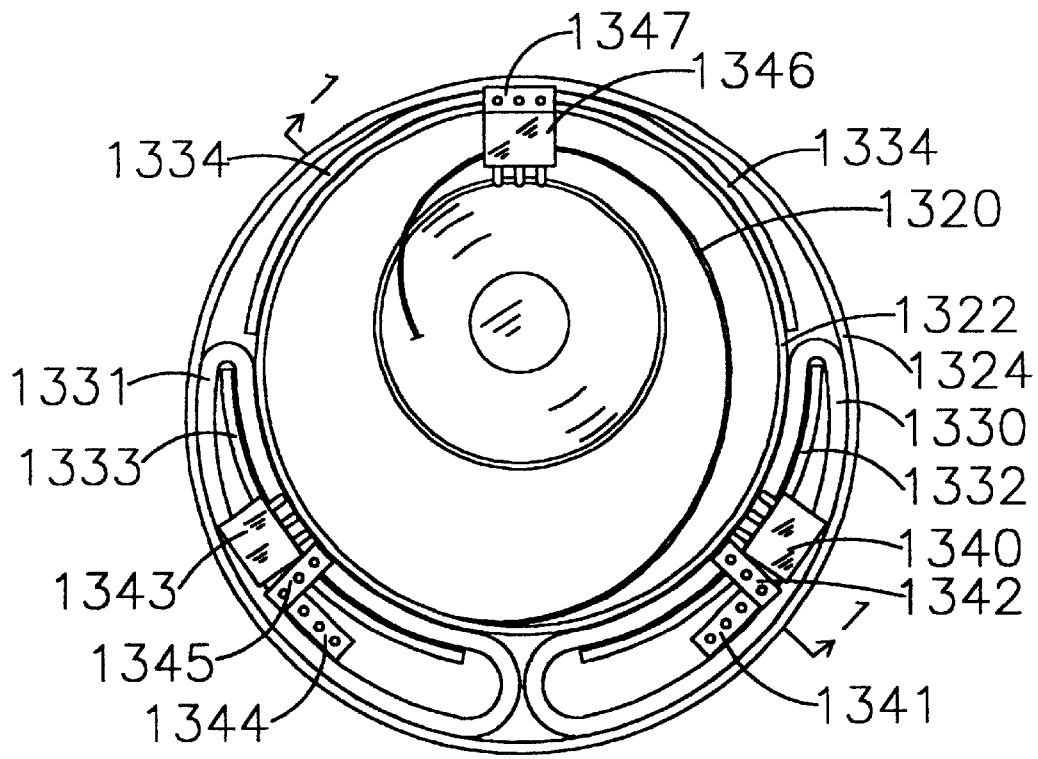
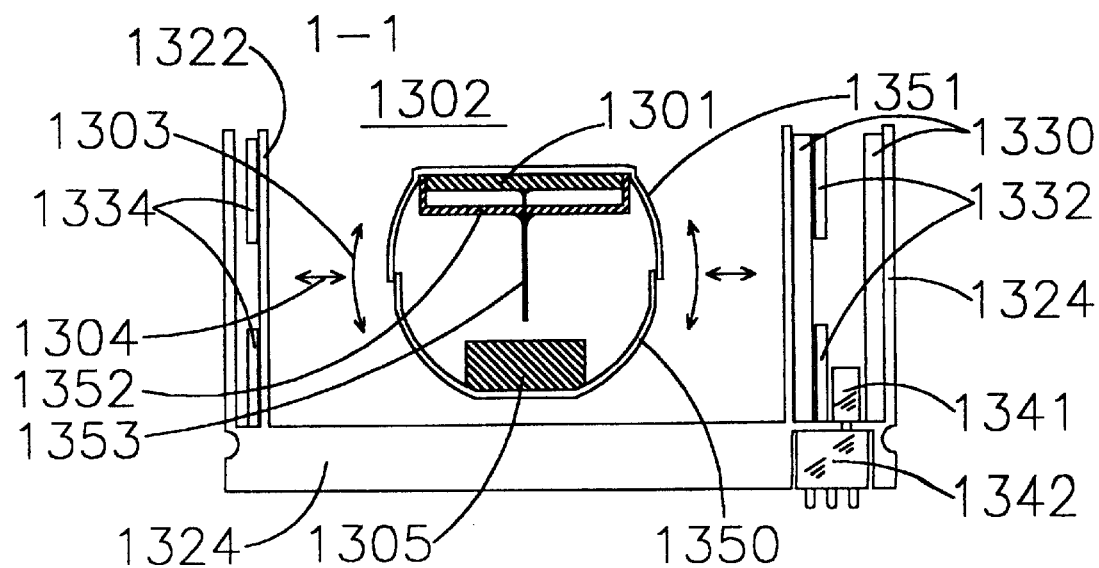

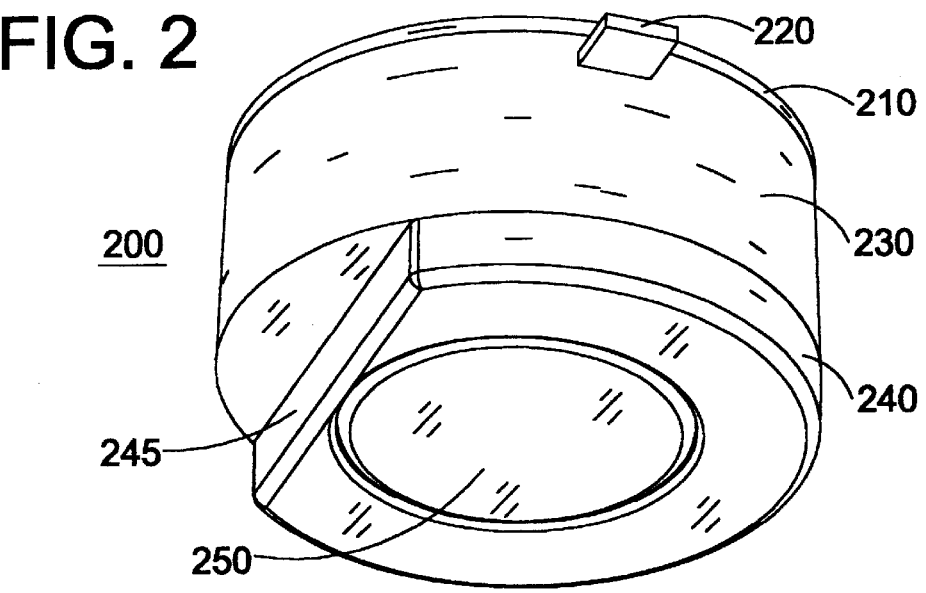
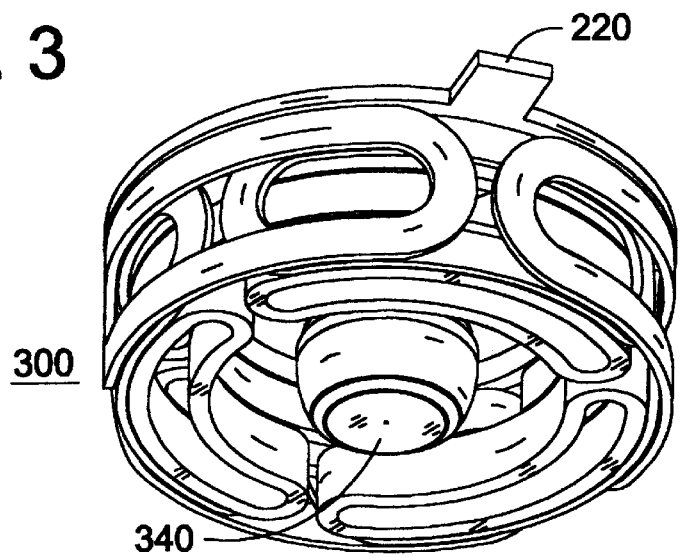
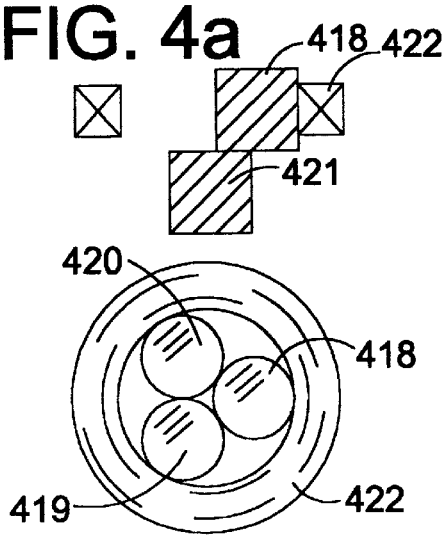
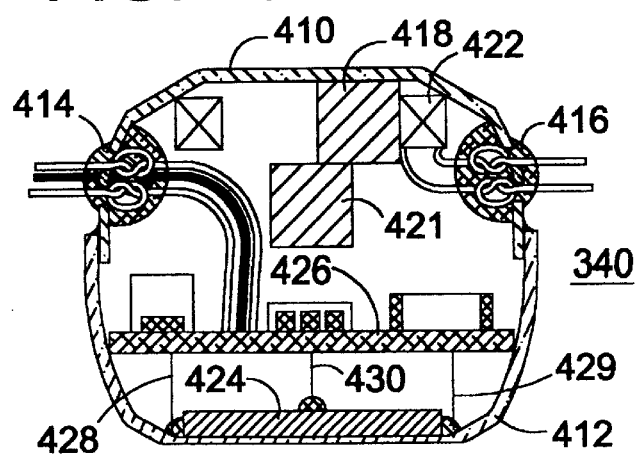

6,131,459

LINEARIZED ULTRASOUND BEAM ALIGNMENT SERVO

BACKGROUND OF THE INVENTION

1. Field of the Invention

The present invention relates to devices for controlling the operation of scanning beam systems. More particularly, the present invention relates to devices for regulating the operation of ultrasonic beam transmitters. Still more particularly, the present invention relates to devices for controlling the positioning and alignment of an ultrasonic beam in two or three dimensions of translation and two dimensions of angular tilt. The invention has particular application in the field of non-intrusive medical analysis devices but is not limited thereto.

2. Description of the Prior Art

The only ultrasound-aiming device of the prior art resembling the present invention is taught by Seale in U.S. Pat. No. 5,844,140: "Ultrasound Beam Alignment Servo." In one embodiment of that invention, illustrated here in FIG. 1, reproduced from FIG. 13 of the prior art patent, Seale teaches a system of air core coils 1330, 1331, 1332, 1333, and 1334, surrounding a water-filled cavity, shown inside cylindrical wall 1322 and above base 1324. The enclosing ultrasound window is removed from the top and not shown, but is normally present and brought in contact with a patient for operation. Within that cavity floats a neutrally-buoyed rotor 1302 containing an ultrasound transducer 1301 and a permanent magnet 1305. The ultrasound transducer is connected to an external ultrasound signal generation and reception system (not shown) by way of a tether cable 1320 of fine flexible wire following a spiral path from the rotor to the side of the water-filled cavity. The magnetic fields produced by the air core coils in the housing exert linear and torsional forces on the magnet in the rotor, causing the rotor to translate and rotate controllably, thereby altering the position and angular alignment of the ultrasound beam from the transducer in the rotor. Magnetic measurements lead to determination of the position and orientation of the rotor, permitting the closure of a multidimensional feedback loop to bring the rotor to a desired position and orientation. The result is to position and align the ultrasound beam emerging from the rotor. One of the potential uses of that prior art system is transcranial ultrasound Doppler, for which an ultrasound transducer needs to be moved in translation and rotation until a partially ultrasound-transparent window is found in the human skull. The ultrasound beam is aligned through this window to insonate a cranial artery with frequency bursts and to receive back Doppler echo signals. Seale's system of the prior art is discussed in some detail here, since the current invention was developed specifically to overcome limitations of the prior art system—limitations severe enough to preclude practical clinical use. The background given here will clarify the context of and necessity for the described improvements. The prior art system in question, while suffering severe deficiencies in an application requiring significant lateral rotor translations in a plane, provides a basis for development of the current invention. In applications requiring levitation of an ultrasound rotor with two-axis rotation but very limited translation, the system of prior art is effective and does not require the invention taught herein. A review of U.S. Pat. No. 5,844,140 provides useful background for the current Specification.

In the prior art, Seale teaches two alternative methods for detecting the position and alignment of the rotor, in order to close feedback loops to control its position and alignment. The first uses an AC magnetic beacon, and the second senses of the field of the permanent magnet in the rotor using multiple sensors in the stator. The DC method will be summarized first, followed by the AC method, in two variations. It will be shown that of the three approaches, only one provides an adequate starting basis for use with a rotor that must translate over significant distances in a plane. The Specification to follow this section will show how severe inadequacies of the most favorable system approach of the prior art are overcome to produce a useful clinical instrument.

The DC field-sensing approach to determination of rotor position/orientation taught in the prior art by Seale takes advantage of inexpensive Hall effect sensors, 1340 through 1347 in FIG. 1. These sensors include a Hall effect bridge circuit responsive to magnetic fields cutting across the plane of the bridge, plus a sensitive amplifier to raise the extremely small bridge output voltage to a useful signal level. This approach was taught as a preferred embodiment for the system most resembling the present invention, and illustrated here in FIG. 1, achieving 5-axis control over translation in x, y, and z, plus tilt of the magnetic dipole axis from a center z-axis direction to give projection into the x and y planes. Because of symmetry, rotation of the rotor magnet about its dipole axis does not affect the detected external magnetic field. Such a rotation cannot be driven by external coils. Thus, rotation about a third axis is not a degree of freedom of the control system in any of the variations described in any detail here or in the prior art reference. Hence, with the exception of systems that might gain control of rotation about a third axis through quadrupole magnetic interactions, most systems for full levitation and tilt control will be 5-axis systems. By using more Hall sensors than the number of degrees of freedom to be determined for rotor position/orientation, e.g., 8 sensors for 5 degrees of freedom in the prior art example shown here in FIG. 1, it was taught to use "redundant" information in the set of magnetic signals to measure and cancel the variable effect of the geomagnetic field and similar steady or varying magnetic fields from distant objects. Specifically, any field whose flux lines are substantially straight and parallel passing through the assembly of FIG. 13 was rejected.

This detection approach to position/orientation works well in practice for rotors that undergo minimal translation, such that the Hall sensors can be located quite close to the levitated rotor. If the rotor translates significantly, and especially if the translation is two-dimensional, covering a significant extent over an (x,y) plane (as in the prior art example shown in FIG. 1), or three-dimensional, covering a significant volume, then of necessity the distance from the rotor magnet to a given Hall sensor varies considerably. As was taught in the prior art, if the coils are to be made compact and are to surround a cavity of significant extent in two or three dimensions, then those coils cannot lift a magnet against gravity without overheating. The solution taught for the overheating problem was to enclose the rotor magnet and ultrasound transducer in a hollow shell, sized to float with neutral buoyancy in an ultrasound transmission fluid, thus offsetting gravity and permitting the rotor to be levitated and moved by very small magnetic forces and torques. Illustrated rotor 1302 of FIG. 1 has the proper proportions for neutral buoyancy. A consequence of this design approach is that the dense rotor magnet 1305 occupies a small fraction of the rotor volume in order to achieve neutral buoyancy, while the rotor itself occupies a small fraction of the volume of the cavity in which it moves. It is well known that the field from a magnetic dipole attenuates inversely as the cube of distance. Hence, the order-of-magnitude of attenuation of the field strength of a permanent magnet, in going from the magnet surface to the surface of the rotor cavity, is on the order of the ratio of the magnet volume to the cavity volume, starting from a magnet surface field strength, which is normally below one Tesla. When the rotor travels from a center position to an edge of its cavity, some of the Hall sensors will end up being roughly twice as far from the magnet, implying an additional 8-to-1 field attenuation. Other sensors, being found more than two times closer to the rotor magnet after a movement of the rotor off center, will see more than an 8-to-1 increase in field strength. Hence, the Hall sensors need to respond with good signal/noise ratio over a dynamic range exceeding 64-to-1. Differential sensitivity of a Hall sensor to change in magnet position varies as the field gradient, which attenuates inversely as the fourth power of distance, i.e. more severely than the field strength itself. Even if Hall sensors were free of noise and drift, which they are not, the large dynamic range indicated here would still present challenges for AND conversion.

Compounding the dynamic range problem is a high noise floor for the sensitivity of solid state Hall effect devices, arising from the physical nature of their detection process. For reasonable current density and tolerable local heating in a Hall sensor bridge, the bridge output voltage is measured in microvolts for field strengths on the order of one Tesla. Thermal agitation establishes a noise floor for the bridge output voltage, regardless of the performance of the amplifier that brings the bridge output up to a useful level. Given the maximum strength of available permanent magnet materials, coupled with the inevitably large magnetic field attenuation factors described above, one finds that a small set of Hall sensors (e.g., the set of eight sensors taught in the prior art patent) cannot accurately resolve the position of a neutrally buoyant magnet-carrying rotor having latitude for significant two-axis translation in a cavity. In the best achievable realization of the system, the levitated rotor is observed to jitter and drift in position and orientation due to disturbances that trace back to temperature gradients across the Hall bridges, to amplifier noise and drift, and to Johnson noise in the Hall sensor bridges. As the rotor moves away from a central position, causing some Hall sensors to operate in a less sensitive range, servo performance deteriorates further.

Low-level position/orientation detection works much better with a beacon coil than by a Hall sensor approach, because of limitations related to the physics of the Hall sensor. Radio receivers routinely detect extremely low signal levels at high frequencies. The drive coils in a levitating servomechanism perform very well as antennas for receiving a beacon signal. In the prior art, Seale taught that the multiple beacon signals received by the multiple drive coils in such a system effectively define non-linear position coordinates for the translational and rotational degrees of freedom of the rotor. In more detail, a beacon coil in the levitated rotor generates a high frequency AC magnetic field, which induces AC voltages in the surrounding drive coils. Each drive coil or set of coils is driven by a voltage amplifier. A transformer wired in series with the amplifier output passes the low frequency drive signal from the amplifier to the driven coil or coils, while high frequency current induced in the coil by the rotor beacon encounters an inductive impedance in the transformer. The AC voltage thus generated and sensed in the transformer secondary winding is amplified and demodulated, using the beacon carrier for synchronous demodulation, resulting in a base band signal that is a beacon coordinate associated with the mutual inductance interaction of the drive coil circuit with the beacon coil in its current position and orientation. It was taught that if the center position and orientation of the AC dipole represented by the beacon coil is conveniently made to match the center and orientation of the magnet or collection of permanent magnets in the rotor, then the strength of the beacon signal induced in a given drive coil circuit is proportional to the strength of the energy coupling between the current in that circuit and a magnetic interaction energy in the rotor magnet or magnet collection. This coupling, measurable with the beacon signals induced in the drive coils and expressible in units of joules per ampere (i.e. joules of magnetic interaction energy per ampere of current in a given coil or coil arrangement), is designated a "beacon coordinate." The derivative of a beacon coordinate with respect to linear position represents a linear force-perampere, while the derivative of a beacon coordinate with respect to angle represents a torsional force-per-ampere. Hence, beacon coordinates map couplings of generalized forces, which are taken to include both linear forces and angular or torsional forces. By proper placement of a beacon coil in relation to a magnet, beacon coordinate mappings correspond accurately to mutual inductance mappings, which forms the basis for measuring beacon coordinates through measurement of induced voltages. Thus, a mapping that forms a practical basis for position measurement can be made almost indistinguishable from a mapping that describes the force couplings used to change measured position.

In the prior art, Seale taught that, even when a system of beacon coordinates is very nonlinear in comparison with, e.g., Cartesian coordinates and tilt direction cosines, one can still close servo control loops with respect to the beacon coordinates of a rotor and achieve a convergent servo system. Furthermore, if there are more beacon coordinates than degrees of freedom of the system, corrective feedback loops through all the beacon coordinates can still be used for servo control in an "overdetermined" system. The advantage of redundant control in an overdetermined system is that even if energy couplings via some beacon coordinates become quite weak for certain rotor positions and orientations, those coordinate couplings that remain strong will dominate the control interaction and can cause the system to converge. Hence, a servo with five degrees of freedom, three in translation and two in tilt angle, can use more than five drive coils, each associated with a beacon coordinate and a servo control loop.

The targets for the beacon coordinates of a rotor can be generated in analog fashion using a joystick system whose beacon coil and detection coils are laid out in the same geometry as the rotor to be controlled. Thus, when the rotor is "asked" to move to the same beacon-coordinate "position" as the joystick, and all the beacon coordinate differences between rotor and joystick are amplified and sent out through the rotor drive coils, then the rotor position will be driven toward a match with the joystick position and can be made to track the joystick. A system accomplishing this has been implemented combining the coil geometry illustrated in FIG. 1 from the prior art with the AC beacon coil approach to determination of the beacon coordinates. The levitated rotor in such a system does in fact track the position of a joystick carrying a beacon coil and inserted into a set of coils matching the coils around the rotor. Problems encountered with that system and overcome with the current invention will be described below. The joystick signal vector, i.e. the collection of beacon coordinates representing joystick position, with possible redundancy, can be generated by computation rather than by direct analog interaction of coils with a physical joystick carrying a beacon coil.

Using the AC beacon approach, a beacon coil in the rotor is excited and caused to generate an AC magnetic field, typically at a frequency well above the mechanical response bandwidth of the servomechanism but well below the ultrasonic range used by the transducer, e.g., 50 kHz. As was taught in the prior art, the beacon coil can be excited by a signal voltage carried to the levitated rotor via a tether cable, of the coil can consist of a shorted conductive loop or shorted winding exposed to an external electromagnetic excitation field, resulting in an "induced beacon." In the induced beacon approach, the detected beacon signal is actually a detected perturbation in the excitation field, caused by the presence of the shorted loop and sensitive to the position and orientation of the shorted loop. If the ultrasound rotor volume is small compared to the volume of the cavity in which the rotor travels, then the "induced beacon" perturbation attributable to the rotor is of necessity weak. The system for determining rotor position is consequently sensitive to perturbing influences other than the rotor, e.g. to eddy currents induced in nearby metallic objects and to magnetic fields induced in nearby ferromagnetic objects. While the induced beacon approach is useful for a rotor confined to minimal translation in a nest of tightly-coupled stator coils, especially where this approach eliminates necessity for a tether to the rotor (e.g. where the rotor acts as a movable reflector of an ultrasound beam), this approach is not useful in the present context of a levitating rotor intended to travel significant distances in translation. Further discussions will therefore concern only beacon coils excited by a signal brought in via a tether wire.

The purpose of the invention to be taught below is to overcome significant problems and limitations of the nonlinear beacon coordinate feedback control system taught in the prior art. The problems concern nonlinearity and singularity in the beacon coordinate system of the device taught for 5-axis control with a large range of translation in an (x,y) plane. In the prior art, it was suggested that signals detected in Hall sensor coordinates could be translated into the beacon coordinates describing the interactions of drive coils and the rotor magnet. As was indicated above, limitations in the Hall sensors preclude high quality realization of the above goal. The system functions, but only marginally. We will therefore concentrate on systems based on an AC beacon coil in a levitating rotor attached by a tether. Detection of position/orientation in such systems is far more robust than with Hall sensors, for two reasons. First, drive coils make excellent antennas for the beacon signal from a levitating rotor, and synchronous demodulation of the resulting antenna signal can be accomplished with excellent linearity, dynamic range, and a low noise floor. Second, inverse-cube-law relations do not apply to the coupling between a small beacon coil and a large and partly encircling drive coil. The inverse cube law applies only to a transmitter and antenna separated by distances significantly larger than the size of either the transmitter or antenna. A drive coil extended in space around a rotor and beacon coil responds to the position and orientation of that coil within a smaller dynamic range than a "point" sensor. Thus, AC beacon signals picked off drive coils are easier to use than Hall sensor signals.

Even given the advantage of coils over point sensors, there is considerable gain variation around a servo feedback loop designed for 5-axis levitation with significant translation. As the beacon coordinate varies with rotor position/orientation, the sensitivity or differential gain for position/orientation detection varies, and the sensitivity or differential gain for actuation, driving changes in position/orientation varies, in the same proportion. The net loop differential gain, being the product of detection gain and actuation gain, therefore varies as the square of the sensitivity of the beacon coordinate to the controlled component of rotor motion. The servo control loop drives an inertial load, meaning that a coil current establishes a component of linear and/or angular acceleration in the load. Such a second order servo system requires some form of damping or phase-lead compensation to achieve good settling to a target position. For precise control of multidimensional position, a component of integral gain is commonly added to the control loop transfer function. "PID" control, for Proportional, Integral, and Derivative components of loop gain, is.described in Seale's prior art teaching. When differential loop gain for a given servo control channel varies widely, however, then a PID control loop behaves poorly. Loop gain variations with changing rotor position alter the "P" "I" and "D" gains by the same multiple, yet among the three gain terms, the proportions yielding the best settling response change as the overall gain changes. The most obvious adverse consequence arises when a controller is optimized for a given gain between beacon coordinate variation and corresponding linear translation or rotation of an inertial mass, and that beacon coordinate gain is reduced. First, the reduction factor is squared, since (as discussed above) the gain reduction hits the control loop twice, once for sensing and once for actuation. A gain reduction causes the system to be underdamped and to have an excessively high integral gain. Both effects contribute to system overshoot and ringing in what would be described as a very sluggish "loose" control loop. An excessive integral component of loop gain can contribute to growing oscillations, and even if recovery from small perturbations converges, integral loop gain can slow overload recovery, especially when the ultrasound rotor bumps a solid surface, leading to blocking oscillations. A high loop gain leads to an overdamped situation, which would not be considered a problem since the time scale of the system response is reduced, so that settling time is not too large. Yet, too much increase in loop gain leads to instability and oscillations at higher frequencies due to higher order phase lags and information delays around the loop. The most obvious higher order phase lag involves coil inductance. At low frequencies, coil drive voltage establishes a proportional current in a coil. At higher frequencies, as inductive impedance in the coil comes to dominate resistance, the coil drive voltage begins to establish the rate-ofchange of current, implying additional phase lag in the control loop. If coil current is controlled by a current amplifier rather than a voltage amplifier, then the gain around the servo loop goes from +6 db/octave for the damping term of the PID controller to +12 db/octave due to the voltage developed to overcome inductance. Information delay arises because position feedback information based on demodulation of a beacon carrier signal comes in pulses with gaps in-between, where position is not being updated. Lowpass filtering of the demodulator output makes the output appear continuous, but this is achieved at the cost of added phase delay. It might appear that carrier ripples propagating through a control loop would be inconsequential. In fact, severe high frequency problems arise if signals approaching half the carrier frequency are not filtered aggressively.

Even though the sluggishness of the mechanical response causes the electromechanical loop gain to fall with increasing frequency even as the electronic gains rise, unintended high frequency couplings come into play. In particular, a demodulator in the system is intended to respond to voltages induced by the beacon coil in a given drive coil. The demodulator also responds to high frequency components coming directly from the amplifier driving the coil. As feedback gains are pushed up, and as phase-lead compensation terms are piled on to maintain good damping at high proportional gains and overcome higherorder phase lags such as inductance, then the gain from the demodulator output around to its own input, via the drive amplifier, increases steeply. A signal at half the beacon carrier frequency, when demodulated against the beacon carrier, produces a new signal at half the carrier frequency. Frequencies below this half-carrier frequency bounce up above half the carrier frequency after demodulation, and frequencies above bounce down below half the carrier frequency. Suppose that one wants a worst-case servo settling speed equivalent to a 5 Hz bandwidth, which is marginally fast enough to not feel sluggish to a human operator. In a highly nonlinear servo controller as taught in Seale's prior art patent, differential beacon coordinate gain with respect to a linear coordinate of position or rotation will easily vary by 20-to-1. This implies a 400-to-1 variation in servo loop gain. Thus, to maintain control to 5 Hz bandwidth in regions of weak electromagnetic coupling, one ends up setting proportional electronic gains 400 times higher than are required for the most sensitive rotor positions. To provide critical damping where beacon coordinate slope is the lowest, one requires phase lead compensation coming into play at the frequency corresponding to the minimum settling bandwidth, e.g., 5 Hz. Thus, one begins to push up high frequency gains starting from a very low frequency. If the phase lead compensation is rolled off with a pole at a moderately higher frequency, e.g., 20 Hz, then the system starts to ring badly around 20 Hz for rotor positions where the beacon coordinate slope is high. As one pushes the lowpass poles up the frequency scale to attain damped servo response and avoid instability at high-gain rotor positions, one quickly reaches a situation where, e.g., with a beacon carrier frequency at 50 kHz, regenerative oscillations are being generated at 25 kHz as drive amplifiers talk to demodulators. Pushing to a substantially higher carrier frequency introduces new problems. When drive coils are packed in close proximity, capacitive couplings between them introduce cross talk. This effect increases very rapidly with increasing frequency. Another constraint for compatibility with Doppler sonar systems is keeping the beacon carrier frequency synchronized with a common denominator of the pulse intervals used for various depths of operation. In a typical transcranial Doppler context, one cannot use a beacon carrier frequency much higher than the 50 kHz range.

The constraints described above imply great difficulties in achieving a servo control system that settles consistently, through its range of rotor positions, even for an equivalent bandwidth of only 5 Hz. The problem concerns primarily regions of low slope of the beacon coordinates with respect to linear coordinates. Even with adaptive electronic gain to avoid problems of excess gain at sensitive beacon coordinate regions, practical limitations in gain around the beacon coordinate servo loop prevent good response.

This problem is compounded by another problem alluded to in Seale's prior art patent, but whose severity was perhaps not fully appreciated: mapping singularity. As beacon coordinates bend, positions in 5-space (for the degrees of freedom in translation and rotation) arise for which the beacon coordinates are far from mutually orthogonal. Singularity arises when no combination of drive signals will produce a generalized force (in a coordinate space of linear and torsional forces) along a particular axis, or cannot generate such a force without simultaneously generating an unwanted force component along another axis. At or near a singularity, a controller cannot control motion independently, or at all, for one or more axis directions. In a prior art coil topology like that illustrated here in FIG. 1, but in a system using an AC rotor beacon coil, coil excitation via tether wiring, and demodulation of induced coil voltages to derive beacon coordinate signals, two singularities appeared in mirror-image positions. They appeared when the rotor was translated to nearly a maximum distance from one of coils 1330 or 1331 and simultaneously tilted such that the magnet in the bottom of the rotor moved, by way of rotation and its off-center location in the rotor, still farther off-center. While experimental observation of the rotor becoming uncontrollable in that region led to a suspicion that the rotor magnet was simply too far from one of the drive coils, a mathematical analysis of the magnetic field structure revealed a true singularity in the matrix of partial derivatives relating beacon coordinates to linear and angular coordinates. With a singularity, all five coils have some "purchase" on the spatial region in question, but no combination of signals from the five coils can provide "purchase" for motion in some particular coordinate direction. In terms of servo performance, motion in that particular direction becomes totally uncontrollable at the singular point and only weakly controllable near the singular point. The same prototype system demonstrated instability when the rotor translated and rotated to bring the magnet and surrounding beacon coil close to the cusp where coils 1330 and 1331 meet. Similar problems have been observed elsewhere near the cusps between abutting coils. It has not been determined whether these are problems of singularity as described above, or problems having to do with extreme curvature of the magnetic fields in a cusp region. In the prior art patent, it was proposed to add redundant coils with associated redundant beacon coordinates and control channels in order to cover the "weak" regions surrounding singular points in the beacon coordinate mapping. Extra coils and control channels were expected to "fill in the gaps" around singularities of a non-redundant system. A redundant coil and associated circuitry to define another beacon coordinate eliminated the mirror-image singularities described just above, but did not eliminate the stability problem near the cusp between abutting coils 1330 and 1331. Whatever further analysis might reveal about this problem, it is clear that the strongly curving fields around cusps between abutting coils, and the corresponding highly nonlinear regions of a beacon coordinate mapping, are best avoided for a well-behaved levitating servo design.

When redundant beacon coordinates are used, problems arise with integral gain in the servo channels. If the servo system can "solve itself" for as many servo coordinates as there are controllable degrees of electromechanical freedom, then the integrator outputs converge to bounded values consistent with keeping the rotor at the desired position and orientation. With redundant coordinates, the system never "solves itself" exactly in all the redundant coordinates, due to inconsistencies between the system than generates targets in redundant coordinates (e.g., a joystick having 5 degrees of mechanical freedom and 6 or more output voltages representing the redundant coordinates) and the actuator/sensor system that is required to match all the channels. For integral control, one must boil the redundant coordinates down to the correct non-redundant number, reflecting the mechanical degrees of freedom. When one does so, the system converges with poor accuracy and repeatability in regions that are nearly singular in the non-redundant coordinates of integral feedback control. Where redundant coordinates are employed, one ends up with extra servo loops and complex blending of non-redundant integral control with redundant proportional and integral control. Redundancy does not solve the problem of very different dynamic responses in different regions of space, with responses in some regions plagued by extreme sluggishness or extreme jitter. As the ultrasound rotor bumps into mechanical limits, in certain regions a bump trips the system into blocking oscillations. Recovery requires shutdown and re-initialization of the servo system, which can be problematic. If the rotor gets too far from its target position in highly nonlinear beacon coordinates, it can get "lost" and fail to find a path to the target coordinates. Even if local singularities in the beacon coordinate mapping are avoided entirely, this is no guarantee of convergence of the rotor from a distance away from a target set of coordinates. Where there is non-convergence, there is usually latchup. The complexity of software control compensations for a highly nonlinear and multidimensional electromagnetic sensing and drive system rapidly becomes unwieldy.

In the prior art, it was clearly believed that a relatively linear beacon coordinate mapping was not feasible in a practical winding topology for a system satisfying the constraints of transcranial Doppler ultrasound. To quote from U.S. Pat. No. 5,844,140, column 12, lines 48–53: "In a concrete example of a rotor for transcranial Doppler ultrasound, where clinical constraints call for windings confined to a small volume asymmetric to one side of the volume of rotor motion, the mapping from beacon coordinates to more familiar and convenient rotor coordinates is highly non-linear and non-orthogonal." The supposed necessity to work with such a mapping led to a system design that worked well only for small excursions from a central rotor position and angular orientation and that failed to function at and near singular points within its intended range. The option of adding redundant control coordinates, as was suggested in the prior art patent, has been shown to yield very limited performance improvements. A way out of the problems and limitations of the prior art system is to accomplish what was thought unfeasible: a mapping of beacon coordinates that are approximately linear and approximately orthogonal over the entire five-dimensional control volume required for applications like transcranial Doppler ultrasound. This is, of course, no merely mathematical mapping, but a description of the geometric electromagnetic performance of a collection of conductive windings. The following specification will show how to create such windings, interconnect them, drive them, and recover signals from them, to achieve such a beacon coordinate mapping. This will be achieved working within the geometric constraint that one side of the ultrasound cavity must be capable of placement on the skin with a side surface very close to the human ear—a constraint believed to necessitate an asymmetric winding configuration. Additional improvements in electronic topologies and methods for position detection and multidimensional servo control will be revealed.

SUMMARY OF THE INVENTION

In accordance with the limitations of the prior art described above, and with the need for an effective and not excessively complicated approach to levitating servo control of an ultrasound rotor in five axes, it is an object of the present invention to define a geometry of multiple coils, multiple drive circuits, and multiple detector circuit pathways, that provide an almost direct linear mapping between the five beacon coordinates of rotor motion control and the five coordinates of Cartesian three-space plus two tilt direction cosine coordinates. In support of that broad object, it is an object to provide dual overlapping sets of coils wherein each set of the dual set provides control over two orthogonal axes of motion or tilt, and wherein each of the two sets overlaps the complementary set in a manner that fills the field gaps where the coils of the complementary set abut. Putting these objects in the broader context of a working servo control system, it is an object to generate the above-described magnetic mappings using multiple overlapping sets of stator coils and using AC coupling measurements between those stator coils and a rotor beacon coil. It is a further object to link these sense mappings to driver actuation mappings, utilizing the same stator coils, thus closing a five-axis servo control loop over the position and orientation of a rotor.

A preferred embodiment of the invention is a five-axis servo for levitating and controlling the motions of a rotor carrying an ultrasound transducer. The purpose of motion control is to aim an ultrasound beam in two axes of tilt and move the origin of the ultrasound beam in two lateral dimensions. Translation control in the third, axial dimension serves to keep the rotor centered vertically in the cavity filled with fluid, which transmits ultrasound between the rotor and an ultrasound window to a patient and also neutrally buoys the weight of the rotor, thus minimizing the electromagnetic force required to move the rotor. Lateral translation of the rotor and ultrasound beam serves to locate an ultrasound-transparent window, e.g., a thin spot in the human skull, and then maintain the beam passing through that window as angular alignment is changed to target various Doppler flow targets on the far side of the window. Since the window lies a few millimeters in front of the rotor, coordination of rotation and translation of the rotor is required to keep the ultrasound beam passing through the same window location while the beam is aligned at various targets. In advancing the levitation technology required for coordinated motions of translation and rotation, with translation covering a relatively large two-dimensional lateral baseline, the present invention provides a way to generate magnetic fields for tilt rotations, and magnetic field gradients for translation motions, such that the fields and gradients are nearly uniform in strength and direction over the range of travel of a magnet and beacon coil inside the rotor. Controllable uniform horizontal fields in both x- and y-axis directions provide linear control of x and y direction cosines of tilt. Controllable uniform horizontal gradients of vertical field strength in x- and y-axis directions provide linear translation control in x and y. Small centering translations of the rotor along the z axis are controlled by the vertical gradient of vertical field strength, whose uniformity is less important than other fields and gradients since vertical position is only stabilized and not changed significantly.

In the preferred embodiment, fifteen coils are used to achieve the fields and gradients just describe. Not all the coils are independently driven, three sets of three being wired together so that each of these sets of three coils shares a single driver/sensor circuit. The wiring together could be series or parallel wiring. Series wiring is preferred as permitting the use of fewer turns per coil of a coarser magnet wire, making coil winding easier. The coils wired in three groups of three control the x and y gradients of vertical field strength for translation. Each of the three driver/detector circuits for these three groups governs a horizontal force along one of three 120-degree axes. Linear force drive signals are translated, effectively by 2-by-3 and 3-by-2 matrix multiplications, in the two directions between orthogonal x- and y-axes and the 120-degree axes of the coils. These matrix multiplications may be performed digitally or may be embodied in gain coefficients of analog summing and differencing amplifiers. The multiple coils used to control translation are overlapped, by offsetting sets of 120-degree axis coils by 60 degrees relative to each other, to reduce the field non-uniformities that occur at the cusps where the ends of coils abut. The nine coils controlling horizontal gradient of vertical field are organized into three layers, top, middle, and bottom, relative to the z axis, with the middle-layer coils offset by 60 degrees of rotation about the vertical axis relative to the top and bottom layers. Within each layer, the coils form an annulus surrounding the rotor cavity, the annulus being split into three angular regions, one per vertical-axis coil. For tilt and vertical translation, x and y horizontal axis fields and the vertical field gradient are controlled by six coils forming two overlapping sets of three 120-degree axis coils. Each coil is a flat pancake, bent to a cylindrical shape, with its magnetic axis pointing radially toward the center of the stator coil assembly. One set of three wraps around the outside of the vertical-axis coils, and the second set of three is wrapped on top of the first set and offset by 60 degrees. Each of these six coils uses an independent driver/sensor circuit so that the coils can be driven with three different patterns of excitation for the three control axes (x-tilt, y-tilt, z-translation) and decoded with respect to three sets of coil-weighting functions to recover position/orientation information in the same three control axes. In terms of matrix translation, as used to describe the vertical-axis horizontal-translation coils, one can describe 3-by-6 and 6-by-3 matrices translating between the control axes of x-tilt, y-tilt, and z-translation and the six driver-detector-coil circuits.

Field and field gradient control in x and y requires more coils using 90-degree axes than 120-degree axes, since a non-overlapped coil set in 90-degree axes requires four coils laid out in two pairs on opposite sides of the rotor cavity in x and opposite sides in y, while a non-overlapped coil set in 120-degree axes requires three coils. For driver/detector circuitry to control x and y translation, a set of four coils in 90-degree axes requires two drivers, one for the series- or parallel-connected pair along x and one for the analogous pair along y, while three coils in a 120-degree set require three driver/detector circuits. When it comes to x-tilt, y-tilt, and z-translation, one does not encounter a comparable saving in driver/detector circuitry for 90-degree axis coils, since a pair of opposite coils along an axis needs to be driven in a differential mode to generate a cross-axis field and in a common mode to generate a vertical gradient of the vertical field. A single driver for the pair will not suffice. While the preferred embodiment uses 120-degree axis symmetry in all coil sets, 90-degree axis symmetry coils could be used to accomplish similar results.

As grouped, the 120-degree symmetry coil sets described above use a total of 15 coils wired to 9 detector circuits, which in turn are mapped to 5 axes of position/orientation. Driving of the coils goes by inverse matrixing from 5 axes to 9 driver circuits to 15 coils. A magnetic dipole in the rotor responds to the driven magnetic fields to produce motion in the 5 axes. The ferromagnetic material for this dipole is a conductive metal in the preferred embodiment. This material is surrounded by a high-frequency beacon coil, whose magnetic fields produce eddy currents in the magnetic metal.

The dipole is therefore constructed from four separate magnets in the preferred embodiment, grouped closely together and aligned magnetically parallel to respond substantially as a single dipole to external magnetic fields, while the subdivision of the magnet substantially reduces the eddy current losses associated with beacon coil operation. It was found that, at a subdivision of one functional magnet into four pieces, eddy current losses at a chosen carrier frequency of 50 kHz were reduced to a lesser magnitude than ohmic coil losses, so that diminishing returns would be obtained by further subdivision of the conductive magnetic material.

The rotor of the preferred embodiment is connected electrically via twin spiral tether cables on opposite sides of the rotor, one cable for ultrasound and one cable for the beacon coil connection. While connection by a single tether works, as described in the prior art, splitting the tether connection function in two leads to more nearly balanced tether forces of the two sides of the rotor. With a single tether, translations and (to a lesser extent) tilt rotations are accompanied by considerable rotations about the dipole axis and ultrasound beam axis, as the tether wraps and unwraps. The coupling of translation and tilt rotation to an uncontrolled axis of rotation leads to a resonant mechanical response that tends to throw a wobble into position and orientation following an abrupt translation or rotation. The balance of a dual tether substantially reduces the coupling to uncontrolled rotation and thus reduces the resonant disturbance to controlled position and alignment.

It was noted in the background discussion that the field strength of a magnetic dipole attenuates inversely as the cube of distance, while the field gradient attenuates inversely as the fourth power of distance. While these power laws apply to magnetic flux across any localized portion of a coil, the averaging of flux interaction over the geometry of overlapping coils described here, and in more detail below, has the effect of canceling the steep power-law variation for the rotor magnet and beacon coil over their limited accessible range inside the enclosure of stator coils. This smoothing, linearizing effect works symmetrically for actuation and detection, as is explained by the symmetry of beacon coordinates as a driver interaction mapping and as a mapping for position sensing. This dual symmetric use of beacon coordinates for driving and detection is explained in Seale's referenced patent of the prior art. Because of this symmetry, a coil and driver design for linearized 5-axis drive leads directly to the coupled and symmetric design for linearized 5-axis sensor mapping.

The use of a beacon coil concentric with and aligned to the dipole moment of a permanent magnet (or group of magnets acting like one magnet) leads to a direct correlation between the AC beacon coupling and the DC energy coupling that defines a beacon coordinate as a ratio of interaction energy to current, e.g., joules per ampere. Two other beacon coordinate detection methods worthy of note share this "direct" correlation quality, one of them approximately, the other exactly.

The approximate method is a variation on the induced beacon approach described briefly above and more completely in Seale's prior art patent, an approach that overcomes much of the sensitivity of the induced beacon approach to conductive or ferromagnetic materials in the vicinity of the coil assembly. The approach is simply to use a beacon winding coupled to a nonlinear circuit capable of converting part of the energy induced into the beacon coil into energy going back into the coil at a different frequency. One can, for example, connect the beacon coil in series with a diode, causing the current flow in the coil to take the form of pulses of a single polarity. The magnetic field from these pulses will have a strong second harmonic of the excitation frequency. This second harmonic becomes the frequency for synchronous detection. To avoid complex interactions of the detection process with the lower excitation frequency, bandpass filtering at the second harmonic frequency and/or band rejection of the lower excitation frequency may precede the detection process. As with the single-frequency induced beacon approach, the strength of the beacon signal will vary as a function of tilt angle. This variation can be compensated in a number of ways. One approach is computational correction based on the received beacon coordinate components. Another approach is a "bootstrap" modulation of the excitation field amplitude to vary in inverse proportion to the computed cosine of the overall tilt angle (which would be the square root of the sum of the squares of the two direction cosine that most simply define the tilt angle.) An alternative harmonic generation method would use two matched antiparallel diodes or two matched opposing zener diodes, depending on the magnitude of the excitation-induced voltage in the beacon coil. The crossover distortion generated by this approach would produce odd-harmonic distortion, especially in the third harmonic, leading to a third-harmonic detection of beacon signals induced in the drive coils. Alternatively, one could operate an oscillator at any frequency, driven by power harvested from the beacon coil at one or more excitation frequencies. These approaches realize their greatest advantage in systems where the rotor is an ultrasound reflector and can thus be operated without a tether when beacon energy is electromagnetically induced in the rotor. By making the beacon frequency emerge from the rotor alone, the position/orientation detection process becomes much less sensitive to small field perturbations caused by external objects near the windings.

The relatively precise alternative to beacon coordinate measurement consists in making the coil in the rotor the detector of AC signals coming from the drive coils. Whereas a single continuous carrier frequency works when the carrier goes to the beacon coil and each stator winding has its own AC voltage detection, the reverse approach demands that AC signals coming from the various drive coils into the one rotor coil have a distinguishing characteristic, such that the signals from various coils can be distinguished. One can place a separate frequency carrier on each drive coil and look for that carrier in the signal received by the rotor coil. By a time-multiplex approach, pulses can be superimposed on the drive coils, e.g., in a regular rotating sequence. In the time slot allocated to each drive coil for excitation, e.g. by a pulse or burst, the detected rotor coil signal is made to contribute to the beacon coordinate measure associated with the excited drive coil. The most obvious implementation would then consist of connecting the rotor coil to a demultiplexing and demodulating processor, e.g. an analog/digital converter feeding data to an appropriate real-time algorithm. Excitation of the drive coils is then accomplished by pulsing the output of each coil driver digital/analog converter in sequence. Hence, one need not implement multiple single-channel detectors, one per coil driver, each one of which is required to reject the coil drive signal while singling out the beacon signal. While this approach is natural where a tether cable is available, a no-tether alternative is possible. In an approach analogous to the harmonic-generating beacon coil described above, the rotor coil can distort or frequency-translate the signals arriving from each drive winding in sequence. The altered signal from the beacon coil circuit may then be detected by one or more stator windings, e.g., by an axial winding dedicated as a receiver for beacon signals from the rotor.

The preferred embodiment of the current invention directs a very sensitive Doppler transmitter/receiver. As will be seen below, the beacon carrier is a low-distortion sinusoid phase-locked to a subharmonic of the ultrasound carrier frequency. Interference between the beacon frequency and the narrow ultrasound Doppler frequency band is carefully avoided. Both harmonic generators and time-multiplexed pulse signals have a potential for interference with the pulse-Doppler signals. Hence, the embodiment to be described below is preferred for its medical end use, though approaches described here are viable and may, in some contexts, be preferred implementations of systems for other end uses.

BRIEF DESCRIPTION OF THE DRAWINGS

FIG. 1 is a prior art illustration, in plan cutaway and side section views, of a 5-axis levitation system for pulsed and Doppler ultrasound applications, especially where controlled two-dimensional lateral translation is needed.

FIG. 2 illustrates, in an oblique view angled upward from below one side, the control head of a preferred embodiment of the current invention.

FIG. 3 shows the same control head view as FIG. 2, except with all housing elements removed, exposing the levitated rotor, the drive coils, and the interconnection circuit board.

FIG. 4a shows plan and elevation section views of the beacon coil and surrounding magnets, while FIG. 4b shows an elevation section of the entire rotor of FIG. 3, incorporating the elevation view of FIG. 4a along with an ultrasound preamp board and the ultrasound transducer with its interference-rejecting connection arrangement to the preamp board.

FIG. 8a is a circuit schematic diagram for a transformer pickup and synchronous detector of beacon signals, while

DETAILED DESCRIPTION OF PREFERRED EMBODIMENTS

Figure 5A:
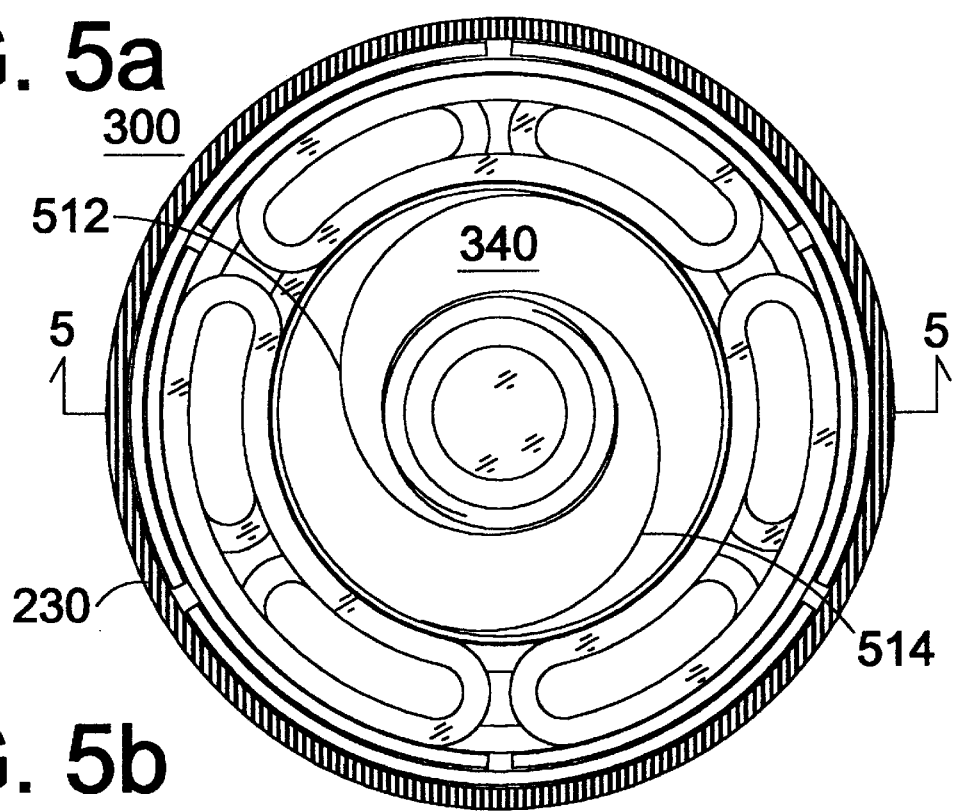
FIGS. 5a and 5b show plan and elevation section views like FIG. 1 but of the current 5-axis levitation system with twin tether cables, multiple radially symmetric overlapping drive coils, and a levitated rotor whose permanent magnet and beacon coil travel in the equatorial plane of the drive coils.

The pertinent prior art concepts conveyed by and along with FIG. 1 are to be found under "Background of the Invention" above in this patent, and in the referenced prior art patent by Seale. The remaining figures concentrate on a symmetric coil topology, using more coils than the system of FIG. 1 and overlapping those coils to produce very smooth electromagnetic fields. The goal is to obtain position/orientation and drive coordinate mappings that approximately match Cartesian coordinates in x, y, and z, plus tilt cosine coordinates in x and y.

FIG. 2 is an external view of the control head, indicating how it is designed to rest on and interface to the head of a subject. The external housing of control head 200 includes cap piece 210, which closes over circuit board 220, of which only the connector tab is visible in this figure. The large diameter portion of the cylindrical housing wall is indicated at 230. Approaching the bottom of the housing piece including wall 230, this piece necks down to a smaller coaxial cylindrical portion that is obscured by overlying pieces in FIG. 2, but which is visible in the side section view of FIG. 5b at 529. This smaller cylinder is closed by flat circular ultrasound window 541 of FIG. 5b. This ultrasound window is covered by an ultrasound-transmitting gel pad 250, as seen in FIG. 2 and in section view in FIG. 5b. Surrounding the cylindrical extension 529 is swiveling base support component 240, a toroid with cylindrical inner and outer walls, flat ends, and a cut-off portion leaving a flat side surface at 245, which is also shown in FIG. 5b. Component 240 snaps onto the neck of the main housing and swivels so that flat 245 can be brought to any desired angle with respect to the cable connection at the visible tab of board 220. Gel pad 250 fits into a recess formed by the inside of 240 and ultrasound window 541 (visible in FIG. 5b) making the bottom. The bottom surface of 240 provides a stable platform resting against a subject's head, while the removed portion of 240 leaving surface 245 makes room for the subject's outer ear. Thus, the gel pad and ultrasound window can be brought quite close to the ear while the control head rests stably on 240. A portion of the drive coils extend out over the subject's hear, beyond and above surface 245. Note that an objective of the prior art design pictured in FIG. 1 was to make the rotor cavity, as bounded by cylindrical wall 1322, far off-center in order to bring the ultrasound rotor close to the ear. The pronounced asymmetry thus enforced on the coil design shown in FIG. 1 created problems relating to the highly nonlinear magnetic field, as discussed earlier. The current invention achieves the clearance for the ear without compromise to the coil topology by raising the coils so that they clear above the level of the outer ear. As is seen in FIG. 5b, raising the level of the coils permits the magnet and beacon coil in the back of the rotor to land in the equatorial plane of the coils, resulting in advantages to be discussed below.

FIG. 3 shows the control head of FIG. 2 with both the external housing and the inner rotor cavity of the housing removed to reveal the working inner components: the drive coils at 300, levitated rotor 340, and circuit board 220 remaining from FIG. 2 except that much of the outer perimeter surface of 220 is exposed in the FIG. 3 view.

FIGS. 4a and 4b show details of the levitating ultrasound rotor. FIG. 4a shows beacon coil 422 surrounding permanent magnets 418, 419, 420, and 421, which are arranged in a roughly tetrahedral pattern with 418, 419, and 420 forming the base and 421 making the top. These four separate magnets replace functionally analogous magnet 1305 of the prior art embodiment shown in FIG. 1. The four separate magnets are magnetically parallel and appear indistinguishable, at a distance, from a single magnetic dipole, axially aligned, and centered at the centroid of the group of magnets. By subdividing the rotor magnet as indicated, the large eddy-current path of 1305 is broken up among the smaller magnets, so that the group of magnets is much less prone than 1305 to dissipate magnetic field energy from the beacon coil. The sides of magnets 418, 418, and 420 may be coated with an insulator to insure that no current circulates around the group of three magnets via lines of side contact. Since these three magnets are magnetically parallel, they repel each other strongly, but winding 422 confines them together in a group, with an adhesive helping to retain the magnets properly together and inside coil 422.

The right half of FIG. 4b shows the side section view of the magnets and beacon coil in the larger context of ultrasound rotor 340, whose shell is made up of two telescoping half-shells, magnetic half-shell 410 and ultrasound half-shell 412. The exterior shape formed when these half-shells are joined is very roughly spherical, except for a substantial flat on the ultrasound end, and a smaller flat on the opposite magnetic end. Radially just outside the flats are conical surfaces whose slope from the horizontal, e.g., 30 degrees, is matched roughly to the maximum intended tilt angle. At this angle, both conical surfaces come against the confining surfaces of ultrasound window 541 and excursion limit surface 543, as seen in the elevation section view of FIG. 5b, these surfaces being gapped so that they limit rotor tilt. Rotor 340 is shown in FIG. 5b at the maximum tilt angle, meeting these limit surfaces.

Continuing with the detailed interior rotor view of FIG. 4b, 414 and 416 indicate areas where electrical connecting wires are brought out through holes in the shell. Adhesive drops at 414 and 416 fill in around the holes on the inside and outside of the shell, securing the wires in the holes and preventing leaks. Each of the wires penetrating the shell is knotted just to the inside of the shell, the knots providing features for the adhesive drops to grip more strongly than straight wire could be gripped. Three wires are shown on the left penetrating the shell at 414, and two wires similarly at 416. The three wires coming via 414 connect inside the shell to the ultrasound circuit board 426, supplying a ground, DC power with a superimposed ultrasound excitation pulse, and the preamplified ultrasound receive signal on the third wire. The two wires coming via 416 connect to beacon coil 422, providing the carrier excitation for that coil. On the outside of the shell, the two groups of wires are connected to spiral tether cables 512 and 514 of FIG. 5—cables visible in the upper sectional plan view, though the external cable connections to the wires penetrating the shell are not shown.

Ultrasound preamp board 426 is connected to ultrasound transducer disk 424 via "hot" wire 430 and dual ground wires 428 and 429. Wire 430 connects to the center of the inside surface of disk 424, this surface being coated with a conductor. The front transducer surface is bonded down to the inside of shell half 412 by a conductive adhesive. Wires 428 and 429 are laid in this adhesive for a short circumferential distance around the edge of disk 424 (this portion not shown) and then bent upward for a vertical shot to board 426 (this portion of each wire shown). A foil on board 426 (not shown) connects straight across from the top of wire segment 428 to the top of wire segment 429. Thus, a conductive ground loop is formed, which can be traced counterclockwise in the diagram from the conductive front surface of transducer 424 on the right via conductive epoxy to wire 429, up to board 426, across the board from right to left via a foil not shown, back down via wire 428 to conductive epoxy and connection to the conductive front surface of transducer 424 on the left, and completing the circuit across the front surface of 424 from left to right. The connection from the back center of 424 via wire 430 to board 426 is made on the board very close to the center of the ground foil connecting at its ends to 428 and 429. The voltage differential between these ground and hot connection points at the middle is preamplified for the return ultrasound signal. The connections just described make a symmetry whereby the portion of the ground loop to the left of 430 matches the area of the ground loop to the right of 430. Thus, a changing magnetic flux penetrating the two sides of the ground loop to the left and right of 430 generates counterbalancing induced voltages, giving null reception of interference at the preamplifier connection. This use of planar coaxial symmetry rejects electromagnetic interference without the necessity of heavy shielding.

Figure 5B:
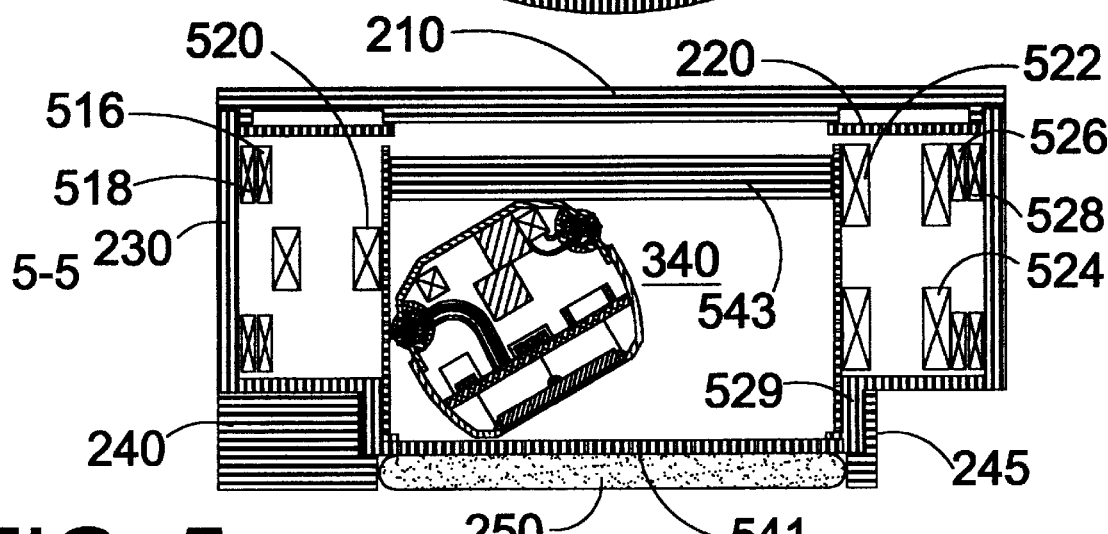

FIG. 5a shows coils 300 from above in a cutaway plan view that also shows rotor 340 as connected by twin spiral tether wires 512 and 514. Note that rotor 340 is drawn in a centered and axially aligned position in FIG. 5a, but not in FIG. 5b, where the rotor has been translated and tilted to the maximum extent. Even though one of the two tethers to 340 needs three electrical conductors for ultrasound, while the other tether needs two conductors for a beacon excitation signal, there are advantages to using an extra wire in the beacon cable so that the tethers are mechanically matched. This matching balances, approximately, the restoration forces acting on opposite sides of rotor 340, so that the rotor is not strongly inclined to rotate about its axial dimension as it moves in translation and tilt rotation. This minimized rotation coupling aids in quicker settling of the rotor to a final beam alignment after an abrupt translation or tilt. The single tether design of prior art experiences a resonance of coupled axial rotation and translation following abrupt movements, with some of this resonant movement coupling into alignment to cause a ringing in tilt alignment response. Servo damping does not effectively kill this resonance, since the resonance principally involves an uncontrolled degree of freedom, with the weak cross coupling into the controlled degrees of freedom generating the resonant settling responses.

Figure 5C:
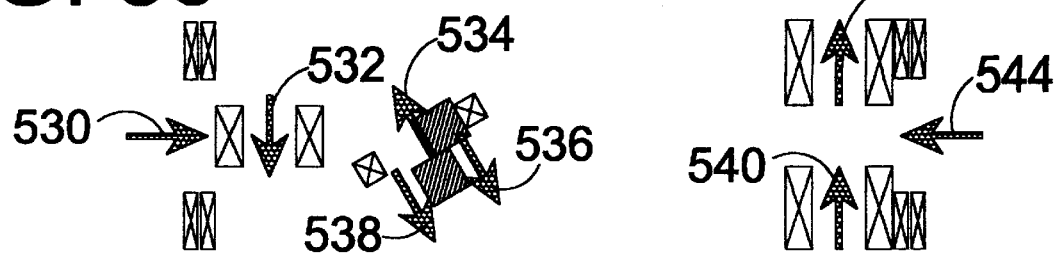
FIG. 5c shows, in a side section view, the principal magnetic axis directions for drive coils, beacon coil, and permanent magnets.

Below the plan view of FIG. 5a, FIG. 5b shows an elevation section view 5—5 of the rotor assembly, as indicated in FIG. 5a. Annular interconnection board 220 is seen below top cover 210. Some of the drive coils are seen in this section. Outer pancake coil 518 on the far left is seen as an "X" in cross-section in over-and-under location where the top and bottom portions of this flat loop cut across the section. Similar over-and-under views are obtained for inner pancake coil 516 on the left, inner pancake 526 on the right, and outer pancake 528 on the right. Three axial coils crossing the section plane are shown as left-and-right pairs of rectangles with internal "X" marks at 520 on the left, in the middle axial coil layer, and at 522 and 524 on the right, in the top and bottom axial coil layers. Additional top and bottom axial coils on the left and a middle axial coil on the right actually cross view 5—5 but are not shown in order to avoid crowding of the image and to place emphasis on the three coils that are shown. The three illustrated coils are wired to function as a group acting along a chosen 120-degree-symmetry axis. Standard winding polarities for these grouped axial coils, and for the pancake coils, are illustrated in FIG. 5c, which shows only coils and a permanent magnet. Each coil has a defined "hot" and "ground" terminal. When the "hot" terminal of a coil is connected to a positive voltage, and the "ground" terminal returned to ground, the resulting plus-to-ground current flow travels around the coil or winding in a rotation sense that defines a vector polarity by the well known right hand rule associating rotation senses with axis vector directions. The head end of such a defined axis vector also defines the north-seeking magnet pole, commonly referred to simply as the north pole, when current flows from plus to minus going from the hot coil lead to ground. While various polarity conventions are workable, one needs to be specified for consistent coil wiring, and such a convention is described here. All pancake coils are wound and connected to have a rotation sense pointing radially from the outside to the inside, as indicated by vectors 530 and 544. Axial coils are wired together with a top and bottom coil on one side, like coils 522 and 524, interconnected with each other and with a middle-layer axial coil on the opposite side, like coil 520. The polarity standard is that the top and bottom coils define a rotation sense, or south-to-north vector, pointing up as shown by vectors 542 and 540. The middle coil has a downward vector sense, in the direction of an axial ultrasound beam, as indicated by vector 532. In the rotor cavity between the coils, and specifically in the equatorial coil-symmetry plane splitting the middle-layer axial coils in half, the magnetic field return path has the opposite direction from the vector through the middle of the axial coil, i.e., pointing up for coil 520 and pointing down for the combination of coils 522 and 524. Thus, a horizontal gradient of the vertical field is established going across the cavity, from an upward direction sense on the left and adjacent to coil 520 on the inside, to a downward direction sense on the right and adjacent to coils 522 and 524 on the inside.

Figure 6:
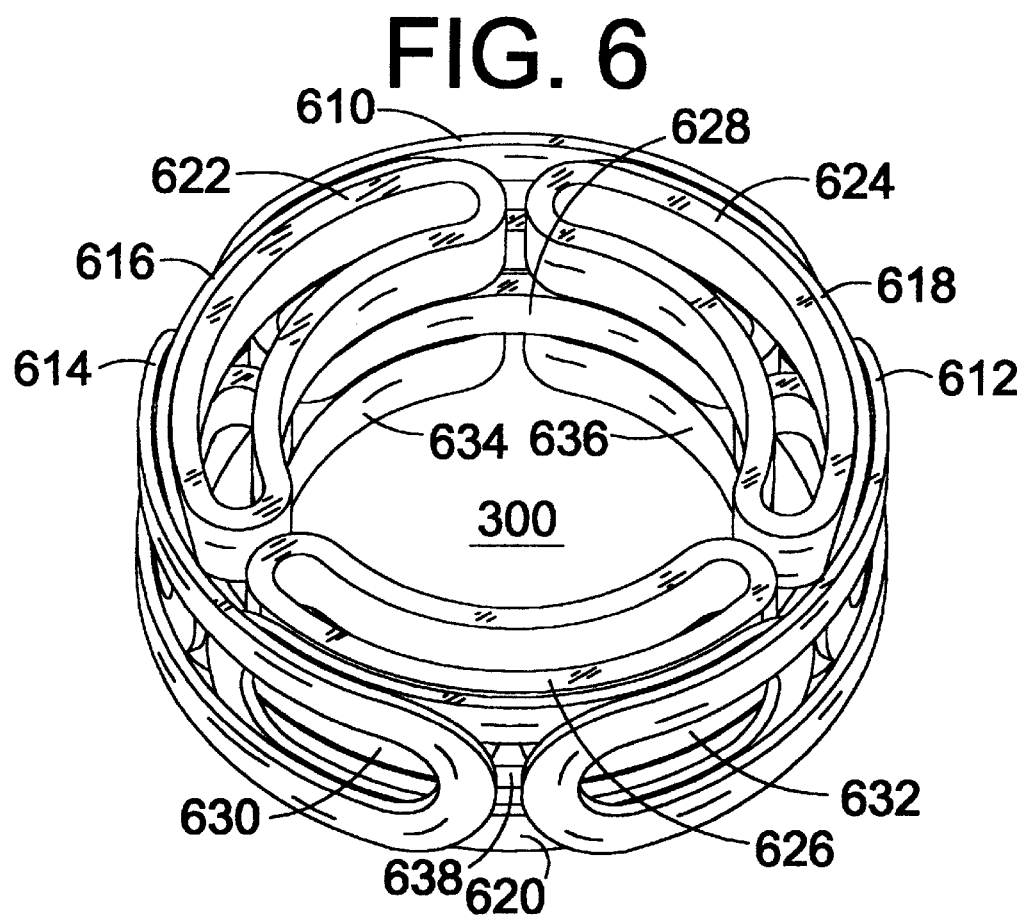
FIG. 6 shows just the stator coils of FIG. 3, obliquely from above, such that parts of all 15 drive coils are visible for identification.

Analysis and measurement both show that, for the overall coil proportions of height and diameter illustrated particularly in FIGS. 5a, 5b, and 6, uniformity of the vertical field gradient is improved by making the middle axial coil shorter and with proportionately fewer windings, than the top and bottom axial coils. For the geometry illustrated, the optimum height proportions are roughly 4:3:4 for top:middle:bottom. If the proportions are 1:1:1, i.e., three identical coils, then the beacon coordinate mapping of a circle around the perimeter of the rotor cavity is distorted into a somewhat triangular shape, with three very rounded corners. With optimum coil proportions, a circle maps to a very slightly distorted circle.

To help understand how coil height proportions affect uniformity of the horizontal gradient of vertical field strength, observe that the field gradient for the top-and-bottom pair of coils weakens in the equatorial plane on approach to the gap between the coils. This top-and-bottom coil gradient is spread out relatively widely going, e.g., from right to left away from coils 522 and 524 across the rotor cavity. By contrast, the horizontal gradient of the vertical field going away from the concave outer surface of a middle coil, e.g. 520, is especially steep coming close to the coil surface and drops off relatively rapidly in gradient strength along a path from left to right. If the top, middle, and bottom coils are made equal in axial length, with the gap between top and bottom coils matching the middle coil length, then the horizontal gradient of the vertical field is too strong near the side of the middle coil, e.g., on the left in FIG. 5*c*, and too weak near the gap between the top and bottom coils, e.g., on the right in FIG. 5*c*. A slight shortening of the middle coil relative to the end coils quickly improves the balance, since the reduction in gap between top and bottom coils reinforces, by strength enhancement near the top and bottom coils, the leveling of gradient strength that takes the form of strength reduction near the middle coil. The top:middle:bottom proportions of 4:3:4 are favorable proportions for the design given here by way of example. For other proportions of the coils involved, e.g. with different ratios of axial depth to diameter across the rotor cavity, the optimum height proportions for the top-middle-bottom coil trio are likely to differ from 4:3:4. In any geometry, however, optimization of the height proportions is expected to yield substantial improvements in linearity. These will be reflected in a more nearly Cartesian mapping of (x,y) positions without compensatory calculations, and which will also be reflected in more uniform dynamic response of the control system over the range of accessible positions.

Standard polarities are indicated for the beacon coil and the permanent magnets in FIG. 5*c*. Vector 534 points up (with a tilt for the rotor tilted as drawn in FIG. 5*b*), indicating an upward rotation sense and south-to-north magnetic sense for standard wiring of the beacon coil. The permanent magnets behave much like current-carrying windings, and their polarity, either by equivalent current rotation sense or by south-to-north polarity, is pointing downward, as indicated by vectors 536 and 538 for magnets viewed and not viewed in the cross-section 5—5.

Figure 7A:
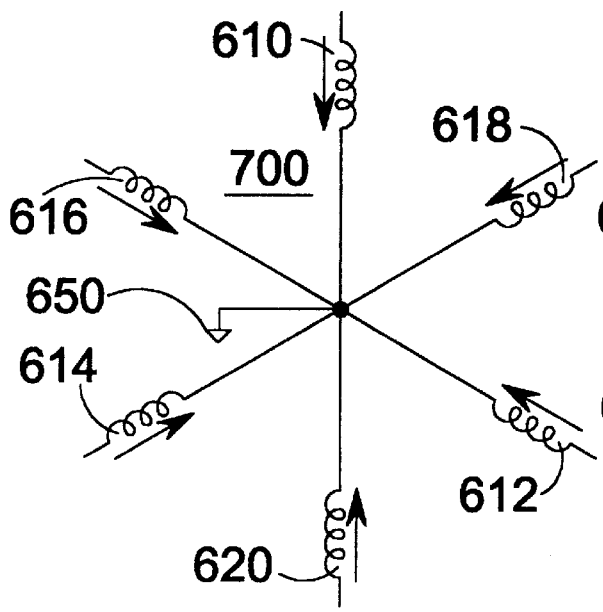
FIGS. 7a and 7b show circuit schematic representations of all the coils shown pictorially in FIG. 6.
Figure 7B:
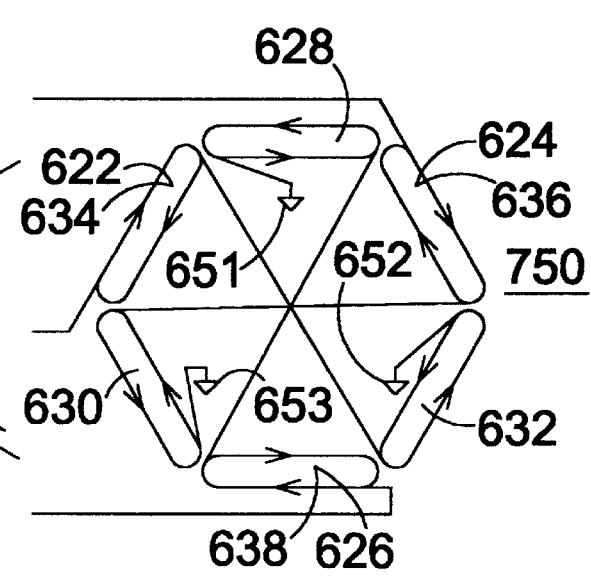

FIG. 6 shows at least portions of all 15 drive coils of assembly 300, while FIGS. 7*a* and 7*b* show the circuit diagrammatic representations of these 15 coils, numbered in the same way. The radial-field pancake coil group of FIG. 7*a* is labeled 700, while the axial-field coil group of FIG. 7*b* is labeled 750. Following the corresponding coils in FIGS. 6 and 7*a*, the outer radial-field pancake coils are 610, 612, and 614 going clockwise from the top in the plan view of FIG. 7*a* or from the far side in the downward-looking oblique view of FIG. 6. The inner radial-field pancake coils are 616, 618, and 620, rotated 30 degrees counterclockwise relative to the outside set in a top-down view. The coil overlaps obtained with the 30 degree rotation using 120-degree symmetry coils leads to a very uniform field distribution for rotor tilt, and to a relatively uniform vertical gradient of vertical field strength for vertical actuation, as discussed below. Middle layer axial coils 628, 632, and 630 match the 120-degree symmetry rotation positions of the outer-layer pancake coils, while the top and bottom layer axial coils are shifted 30 degrees about the axial direction relative to the middle coils. In FIG. 7*b*, respective top and bottom coils 622 and 634 in the 60 degree position (counterclockwise from vertical) are labeled for the same current loop, since they lie on top of each other in that projection, and similarly for coils 624 and 636 in the −60 degree position and coils 626 and 638 in the 180 degree position. In FIG. 7*a*, the coils are diagrammed with hot leads pointed out and a shared center ground at 650, with arrows indicating the inward-directed coil winding sense explained above. The schematic representation ignores the actual circumferential geometry of the coils and highlights the radial directions of the coil fields as experienced on radial lines through the coil centers. In FIG. 7*b*, coil axis vectors point perpendicular to the plane of the diagram, so standard rotation senses are indicated by arrows going around the coil loops in clockwise (for a vector sense down into the page) and in counterclockwise (for a vector sense up out of the page) directions, based on a top-down view. Just three wires are shown coming in from unseen drivers on the left, each wire connecting to a top and bottom coil pair and then connecting across to a single middle coil, grounded on the other middle coil lead. Three axes are thus identified in terms of pairs of coils, going from the hot lead side and a negative (clockwise) rotation sense pair of top and bottom coils to the ground lead side and a positive (counterclockwise) rotation sense middle coil. Thus, the uppermost hot lead connects into the series top-and-bottom pair of coils 624 and 636 with negative current rotation, with further series connection to center coil 630 with positive current rotation, and with final termination at ground 653. An axis associated with this coil pair and arbitrarily identified with a vector pointing from the negative-rotation-sense coil to the positive-rotation-sense coil, points at an angle of 210 degrees with respect to zero degrees as horizontal to the right. Similarly, the middle hot lead connects to top and bottom coils 622 and 634, from there to middle coil 632, and from there to ground 652, with the associated vector direction being 330 (or −30) degrees. Finally, the bottom hot lead connects to top and bottom coils 626 and 638, from there to middle coil 628, and from there to ground 651, with the associated vector direction being 90 degrees. Since the magnetic field just external to the inside of one of these coils points in the opposite direction to the coil rotation sense (based on a positive hot lead), the horizontal gradient of vertical field strength in the space between the coils actually points in the opposite direction from the identified axis, i.e. at angles of 30 degrees, 150 degrees, and 270 (or −90) degrees, opposing the axes identified in sequence above with the angles of 210, 330 (or −30) and 90 degrees. The diagrams of FIGS. 7*a* and 7*b* are reused in the schematics of FIGS. 10*a* and 10*b*.

It should be noted that capacitive couplings between the drive windings shown in FIG. 6 can cause significant perturbations in beacon signals received by the windings. These effects are minimized by putting extra insulation to gap adjacent coils where they fall in contact over large areas. Such insulating gaps are important primarily for adjacent cylindrical surfaces, between the inner and outer layer of pancake coils, and between the outsides of the vertical-axis coils and the inner pancake coils. Such insulating gaps need not be very large, e.g. 0.1 to 0.2 mm (0.004 to 0.008 inches), and can be provided using tape or by coatings applied to the surfaces of the windings prior to assembly.

Figure 8A:
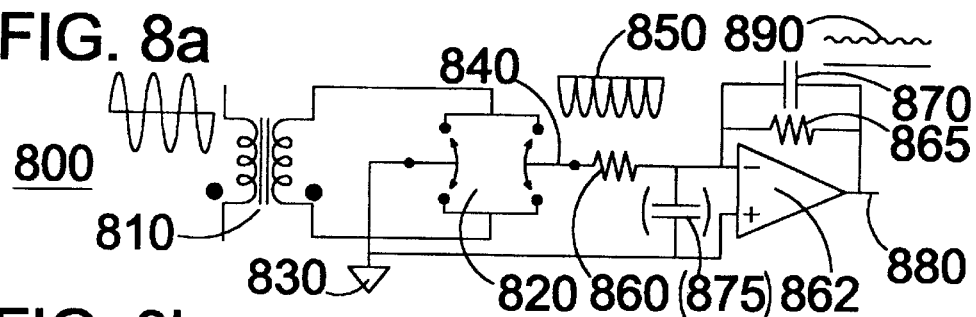
Figure 8B:
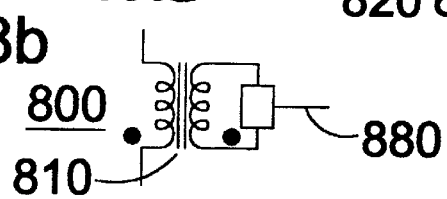
FIG. 8b shows the icon used to represent this circuit in the larger system schematic of FIGS. 10a and 10b.
Figure 10A:
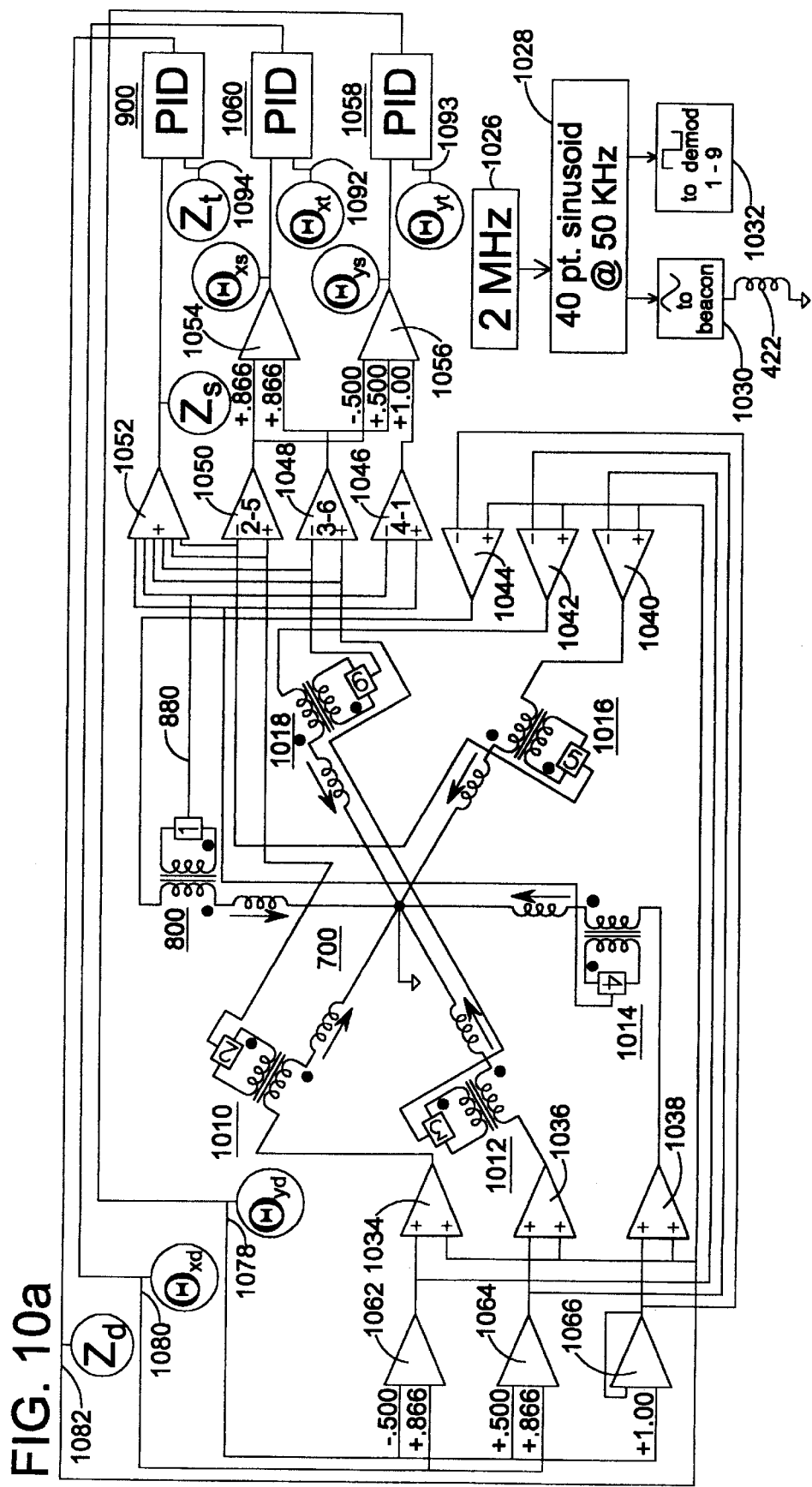
FIG. 10a is a circuit schematic representation of the part of the servo system controlling tilt in two axes and translation in the vertical axis. These three degrees of freedom are controlled using six overlapping coils in two layers with six independent drivers and six beacon signal detector channels. The circuitry includes matrix mapping between the three degrees of freedom and the six drive/sense channels. The schematics of FIGS. 10a and 10b are intended for conceptual presentation rather than direct implementation "as is" since many summing and differencing functions can be implemented with fewer electronic components, at some expense of obviousness in reading the schematic.
Figure 10B:
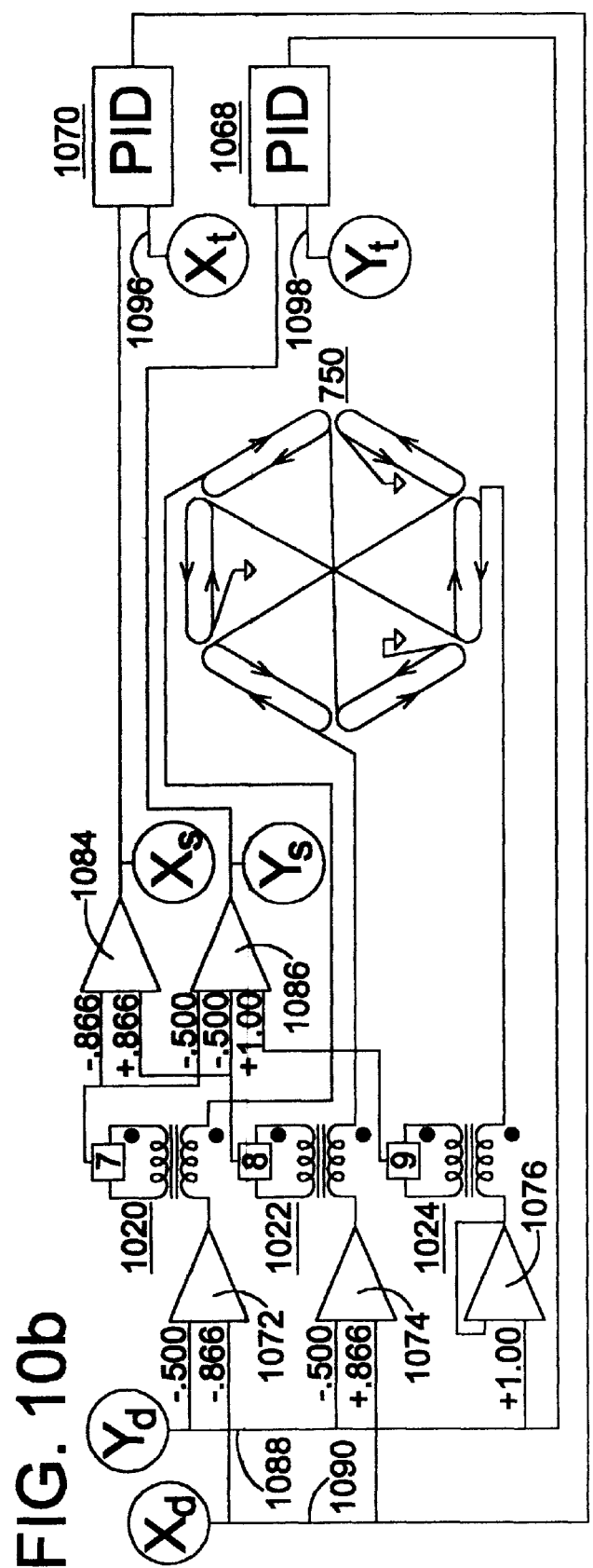
FIG. 10b is a continuation of the schematic of 10a, showing the two lateral translation degrees of freedom as mapped to and from three drive/sense channels, with each one of the three channels using three series-wired coils.

FIG. 8*a* shows the circuit that is used to pick off and demodulate beacon signals from the nine coil-drive circuits of FIGS. 10*a* and 10*b*. FIG. 8*b* shows the abbreviated circuit symbol used in FIGS. 10*a* and 10*b* for the circuit of FIG. 8*a*. The circuit schematic of FIG. 8*a* and the abbreviated representation of FIG. 8*b* are both labeled 800, since they identify the same thing. Examining FIG. 8*a*, a signal containing low frequency content down to DC comes from a driver amplifier, not shown here but shown nine times in FIGS. 10a and 10b, connecting to the upper left lead of transformer 810, the primary connection opposite the polarity dot. The dotted end of the primary, on the lower left, connects to a drive coil. Thus, all currents flowing in the series circuit of the driver amplifier output and the driven coil pass through the transformer. Beacon signal voltages induced in the drive coil appear across the primary of transformer 810, attenuated by a factor depending on the primary impedance of 810 and the impedance of the driven coil. This attenuation depends on the loading of the secondary winding of 810, whose description can be quite complicated since this loading includes a demodulator switching circuit, to be described below. The function of transformer 810 is to pass the low-frequency drive signal at a very low impedance while capturing the carrier-frequency signal coming back from the driven coil, e.g., at 50 kHz, and transferring this signal to the secondary winding for synchronous demodulation. The sinusoid waveform shown to the dotted lower left side of 810 represents the carrier signal voltage coming from the drive coil. When the transformer secondary is in a no-load or open circuit condition, the primary impedance is almost purely inductive and is the sum of the mutual inductance plus the much smaller primary stray inductance of the transformer. Under the open-secondary condition, the drive coil and the transformer primary act like an inductive voltage divider, such that the beacon voltage induced in the drive coil is attenuated by the ratio of transformer primary inductance to the sum of the inductances of the transformer plus the coil. Transformer 810 is typically designed so that when the right-hand secondary is open-circuited, the primary and the drive coil have roughly the same inductance, leading to a signal attenuation ratio of about 0.5. If the transformer inductance is reduced from an impedance match, the voltage transfer is reduced and the beacon signal is not captured efficiently, while raising the transformer inductance above an impedance match yields diminishing benefits as the attenuation ratio approaches a limit of 1.0. Transformer tradeoffs are considered in more detail below. The transformer turns ratio can be set as desired, altering the voltage and impedance levels of the secondary output relative to the primary. A turns ratio of 1-to-1 is appropriate for this type of design. A pair of electronic switches, e.g., field effect transistors operated in switching mode, is indicated at 820. Not shown is the gate control circuitry, which causes these switches to switch oppositely in double-pole double-throw fashion, creating a reversing connection between the transformer secondary leads and the two switch output leads, one of which goes to ground 830 while the other goes via switch output lead 840 to resistor 860. Resistor 860 goes to the input of inverting op amp 862, whose feedback includes parallel-wired resistor 865 and capacitor 870. The non-inverting side of the op amp is returned to ground 830. The op amp output voltage appears on output lead 880, which is indicated in FIG. 8b as well as 8a. To the extent that the op amp maintains its inverting input at a virtual ground, the transformer secondary is loaded by the resistance of 860, as viewed through the frequently reversing connection of switch assembly 820. With a resistive load, the apparent load resistance reflected by mutual inductance to the transformer primary is resistive, despite the polarity reversals of switch 820, since the resistor obeys ohm's law instantaneously, regardless of connection polarity. If inductive or capacitative impedance components enter the load equation, then the reversals of switch 820 do affect the load reflected at the transformer primary, because the load then retains "memory" of the signal polarity that was applied to it prior to a reversal of switch 820. Consider the case where op amp 862 is not overloading and is functioning with sufficient gain-bandwidth to maintain its inverting summing junction substantially at ground potential, causing the transformer loading by 860 to appear resistive. Suppose, also, that switch 820 is driven in the correct synchronous phase relative to the beacon carrier. Then the output voltage from the switch appearing at 840 and applied to resistor 860 will have the appearance of waveform 850, a full-wave rectified sinusoid rippling, e.g., with negative-polarity lobes below a baseline voltage of zero volts. In a practical circuit, switching transient glitches and voltage wobbles from amp 862 maintaining an imperfect virtual ground will result in some alteration of the idealized waveform shown at 860. The parallel resistor-capacitor combination in the feedback of the op amp results in an inverted, lowpass-filtered version of waveform 850 appearing at output 880, such as ripple waveform 890, which is drawn above a straight reference line indicating ground potential.

Concerning impedance matching and the design of transformer 810, when the primary-winding inductive impedance of 810 (with open secondary) is raised in an effort to maximize signal capture, design for high inductance causes problems. Ignoring problems of core size, an excessive transformer inductive impedance adds series inductance and resistance to the path from the coil drive amp to the drive coil. The series inductance slows the response of coil current to track coil voltage and thereby produce a magnetic field in the coil. This inductive lag slows the response of the electromechanical servo loop. In terms of transformer design, the low frequency currents passing through the transformer on the way from the driver amp to the coil, including DC current components to hold steady rotor position, set up magnetic fields in the transformer core having the potential to saturate the core. An effective design for transformer 810 employs a relatively large pot core (e.g., a standard 11 mm. diameter) with a fixed air gap. The air gap lowers the mutual inductance of the pot core for given numbers of winding turns in the primary and secondary, thus lowering the ratio of core flux to winding current and helping to avoid saturation. To meet a specified primary inductance target (with open secondary), e.g., to match the inductance of the drive coil, the designer can use a few transformer turns with no core air gap, more turns with a small air gap, or still more turns with a larger air gap. As the transformer design progresses toward more turns with larger air gaps while maintaining the same inductance, the ratio of core magnetic flux to winding current goes down, implying a higher winding current threshold when the core reaches saturation flux. Eventually, at very large air gaps and many turns, the ohmic resistance of the transformer winding becomes large enough to present a problem. The designer arrives at a sufficiently large pot core with a sufficiently large air gap to satisfy the triple requirements of 1) DC winding resistance lower than the drive coil, 2) primary inductance (with open secondary) roughly equal to drive coil inductance, and 3) a saturation current exceeding the maximum drive current by a sufficient margin to maintain moderately linear response, typically a margin of 2-to-1 or more below saturation.

A final consideration in assuring that a transformer design is acceptable is linearity. When a low-frequency drive current creates a significant field strength in the transformer core material, even if that field strength is significantly below saturation, e.g., only 50% of saturation, the magnetic permeability of the core material varies in relation to the low excitation amplitudes and the moderately high frequency of the beacon carrier signal. The transformer therefore causes intermodulation distortion, where a low-frequency drive current of either polarity reduces high-frequency low-amplitude core permeability, thus reducing the mutual inductance that moves the carrier signal from the primary to the secondary. A possible effect is described in the following scenario. The servo control loop moves the rotor into contact with a cavity boundary, where motion stops. The formerly closed servo loop opens up as the position error is not resolved and the residual error is amplified, pushing one or more drive amplifiers into clipping. The increased drive current flowing through the affected coils pushes the associated transformers to higher field bias, which reduces inductive coupling and thus reduces the beacon signal transferred to demodulation circuitry. The servo loop then "thinks" that the rotor has moved closer to the center position, which increases the position error signal, thus maintaining the driver amp or amps in clipping. As the target position is moved back from the location of the mechanical boundary, an unresolved error signal persists until the target position has moved inside the incorrect apparent rotor position, which was moved closer to the center of the housing by the influence of increased overload current and intermodulation distortion. When the target position is backed sufficiently far from the boundary, the servo loop snaps out of latchup and the rotor jumps inward to resume tracking the target position. Hence, an intermodulation distortion due to magnetic nonlinearity not only distorts the mapping of positions, it also causes the rotor to hang up when it bumps a boundary, with release from the hangup occurring only when the operator or controlling computer moves the control target position back sufficiently toward a neutral or center position.

Two effects mitigate transformer core nonlinearity. First consider the core constant, often designated AL and typically having units of nanohenrys per 1000 turns. A core constant value for the ungapped version of the core will provide a measure of the magnetic reluctance associated with the nonlinear core material. As regards coupling of a small carrier signal in the presence of a large low frequency or DC signal, the core constant defines the mutual inductive impedance that "captures" the beacon signal and carries it to the demodulator. At core saturation, the effective core constant for small signals is reduced nearly to zero. Very roughly speaking, the fractional reduction in the core constant is of the same order of magnitude as the fraction of saturation reached by the core. When a core gap is introduced, the core constant is reduced, the reduction being driven by the linear magnetic reluctance of the air gap acting in series with the nonlinear magnetic reluctance of the core. If, for example, the core constant is reduced by an air gap to 20% of the no-gap value in a gapped core, or 5-to-1, then roughly 80% of the reluctance is linear air-gap reluctance, while the remaining 20% is the nonlinear core reluctance. Hence, for fractional core non-linearities below 50%, the effect of those core nonlinearities will be attenuated by about 5-to-1 by the superimposed linear air-gap reluctance. (By analogy, one can think of the linearizing effect of negative feedback through linear resistors around a nonlinear amplifier, such that reduction in closed-loop gain is accompanied by increasingly linear closed-loop response.) When the core approaches saturation and core reluctance skyrockets to exceed the air gap reluctance, then the signal coupling across the transformer falls rapidly despite the linearizing air gap effect. (Returning to the amplifier analogy, when the amplifier clips, no amount of linearizing feedback will prevent the distortion from showing up at the output.) It is seen that for operation below 50% of core saturation, an air gap linearizes signal transfer through the transformer roughly in the ratio of the reduction of the core constant by the air gap.

The second distortion-mitigating effect is using a low load resistance at the transformer output. If resistor 860 is reduced to a small value, then the transformer will operate in a current mode at the carrier frequency, while continuing to operate in a voltage mode at frequencies so low that the inductive impedance of the transformer secondary (as determined for an open primary) falls below the net resistive impedance in the secondary circuit. (Note that excessive reduction of resistor 860 can cause op amp stability problems relating to transformer winding capacitance coupling to the op amp inverting input.) When a transformer operates in current mode, ampere-turns of current in the secondary winding cancels the ampere-turns associated with the primary, so current signals are transferred with minimal effect on core magnetic flux. In a current mode, the current transfer ratio varies inversely as the turns ratio (i.e., a voltage step-up ratio is a current step-down ratio) largely independent of mutual inductance, as long as inductive impedance significantly exceeds the small ohmic impedance of the winding and resistor 860. One might expect problems with op amp input offset voltage if resistor 860 is reduced to zero or nearly zero, but this is not the case. DC currents flowing from the op amp summing junction to ground 830 via switch 820 must pass through a winding whose terminal connections are constantly being reversed. Thus, the DC current encounters the impedance of the transformer not at DC, but at the carrier frequency driving switch 820. If, conversely, a DC current flows through the secondary winding of transformer 810, this is seen at the op amp input as a carrier-frequency current. Offset currents due to op amp input offset see, via switch 820, the carrier-frequency impedance of the transformer, including stray secondary inductance and the impedance on the primary side, including drive coil resistance, reflected on the secondary through the coupling of mutual inductance. Operation in a current mode is thus seen as a means to reduce problems associated with transformer nonlinearity, recognizing that the transformer must nevertheless be designed to avoid core saturation at maximum coil drive currents. Current mode operation takes place only above the frequency threshold where inductive impedances dominate over resistance. In the bandwidth of operation of the rotor-controlling servo, most of whose activity is below 10 Hz, even a short across the secondary winding has little effect on transformer core flux arising from currents in the primary.

It is seen that the details of the design of the circuitry of FIGS. 8*a* and 8*b* leave many options and variations on the theme presented, with transformer design and mitigation of transformer nonlinearity being important issues. The inverting amplifier topology shown by way of example here was chosen for its flexibility and ability to demonstrate current-mode operation. A non-inverting topology is also feasible, in which resistor 860 connects to a capacitor 875, where both this capacitor and the number are drawn in parentheses to indicate an alternative topology. The opposite lead of 875 is grounded to 830, yielding a passive RC lowpass filter whose output is readily amplified in voltage mode. In this case, inverting op amp 862 and feedback capacitor 870 are omitted, while resistor 865 becomes zero ohms, i.e. a direct connection to output 880. This output 880 is used, either directly or with amplifier buffering, to drive inputs of the sort illustrated in FIGS. 10a and 10b. An advantage of the passive RC topology is that switching transient energy is filtered effectively to very high frequencies by the passive RC topology, so that transients do not reach an op amp input, thus avoiding input overload problems and distortion-related offsets. Modalities including inverting voltage mode, inverting current mode, non-inverting passive voltage mode (i.e. passive RC filtering) and various others can be made to work, when designed by one skilled in the art.

Figure 9A:
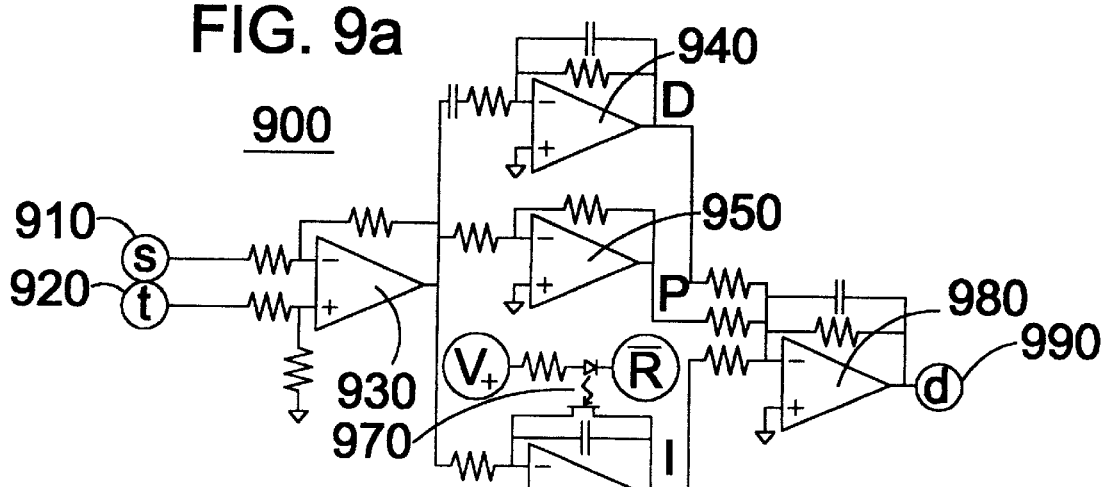
FIG. 9a is a circuit schematic diagram for an implementation of a "PID" transfer function, with integral reset, for a single channel of servo feedback, while FIG. 9b, like FIG. 8b, shows the icon representing this circuit in FIGS. 10a and 10b.
Figure 9B:
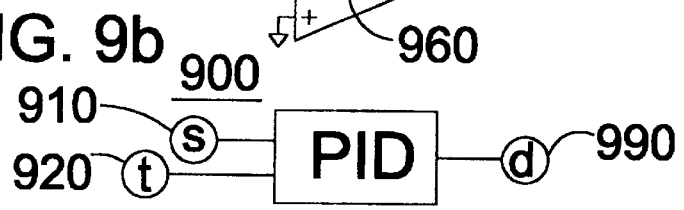

FIG. 9a illustrates one possible topology for a conventional PID controller, labeled 900, five of which operate for the five degrees of freedom of the servo system illustrated in FIGS. 10a and 10b. FIG. 9b illustrates the abbreviated schematic symbol for the circuit of 9a, or an equivalent circuit, where the abbreviated symbol is used in the schematics to follow. The topology of FIG. 9a uses separate op amps for separate components of the PID transfer function, facilitating explanation as well as adjustment, though not minimizing component count. The PID circuit uses two inputs, 910 and 920 (seen in both FIGS. 9a and 9b), respectively labeled "s" for sensed signal and "t" for target signal. Op amp 930 and associated resistors provides, as output, the difference of the target and sense signals. The resulting difference signal is applied to three inverting op amp circuits built around amplifiers 940, 950, and 960, providing the respective derivative, proportional, and integral terms of the PID transfer function. The integration circuit built around op amp 960 includes a reset circuit built around an optically isolated field effect transistor switch, which can short the integration capacitor. This reset function, driven by control logic that monitors for overload conditions, is useful for speeding recovery from overload or latchup conditions occurring when the levitated rotor bumps into an excursion limit. The three outputs from the inverting band-limited differentiator 940, inverter 950, and inverting integrator 960, are summed by inverting summation amplifier 980, whose feedback includes a capacitor for lowpass filtering. This lowpass pole is typically set to attenuate at the carrier frequency and above, leaving the servomechanism bandwidth relatively unaffected. The output of 980 is shown at 990 in both FIGS. 9a and 9b, and labeled with "d" to indicate the use of this output as a "drive" signal. For use in operating drive coils, this "drive" signal must be matrixed in combination with other drive signals into the multiple signals, e.g., the nine signals in the preferred embodiment being described, to power the drive coils. Similarly, sensed beacon carrier data needs to be mapped back from the multiple drive and demodulator circuits (e.g., nine such circuits) to the five PID circuits for comparison with the corresponding five target signals. The circuitry of FIGS. 10a and 10b shows this return path of beacon carrier data starting with nine channels of demodulation followed by matrixing from nine to five signals. It is feasible to capture the beacon-frequency signals from the nine driver circuits, matrix these signals from nine to five, and then use five demodulation circuits instead of nine—although the demodulators then become separated from the transformers of the FIG. 8a topology, requiring a different circuit design. Note that capacitive couplings between the drive windings can cause cross couplings and phase shifts among the beacon signals. Combining beacon signals at the carrier frequency before demodulation will result in different phase-shift artifacts than would arise with demodulation coming before matrix combining to reduce the drive channel signals down to the five degrees of freedom of the levitated rotor.

FIGS. 10a and 10b combine the transformer/demodulator circuit schematic symbol of FIG. 8b, the PID circuit schematic symbol of FIG. 9b, and the schematic coil layout representations of FIGS. 7a and 7b, to provide an overall servomechanism schematic layout. The preferred embodiment of the system operates with a 2 MHz pulsed Doppler ultrasound imaging system, whose carrier at 1026 (lower right of FIG. 10a) is applied as synchronization to a digital function generator circuit, 1028. This circuit has count-down logic to generate 50 kHz signals at an exact subharmonic of the 2 MHz carrier, the same subharmonic that serves as a common denominator for varying pulse intervals in the Doppler ultrasound system. This phase synchronization avoids some artifacts associated with shifting phases of cross-talk interference between the pulsed Doppler system and the servo system. Two 50 kHz signals emerge from 1028, one being a square wave indicated at 1032, used to drive the switches like 820 in the synchronous demodulator circuits. The second 50 kHz signal is a sinusoid, indicated at 1030, which is applied to beacon coil 422, shown schematically in FIG. 10a by the circuit symbol for an air core coil. This sinusoid is constructed using digital/analog synthesis of a sinusoid, e.g., using a 2 MHz update rate for a 40 point digital waveform of a single sinusoidal cycle, resulting in a 50 kHz synthesized sinusoid. An analog lowpass filter is used to remove high frequency transient energy from the synthesized sinusoid, resulting in a smooth sinusoid with good stability and low distortion. The demodulation square wave at 1032 is phase adjusted, relative to the sinusoid from 1030, to match the phase of beacon signals reaching the demodulator signal inputs. The magnetic field from beacon coil 422 interacts with the six drive coils of FIG. 10a and the three series sets of three drive coils of FIG. 10b, while square wave 1032 is used in the six demodulator circuits of FIG. 10a and the three demodulator circuits of FIG. 10b.

Starting examination of FIG. 10a at the six radial-axis pancake drive coils of assembly 700, here shown without the labeling of FIG. 7a, one may identify the coils by their angles relative to a horizontal vector extending to the right. The 90-degree coil, directly above the center ground point, is shown connected to pickup and demodulator circuit 800 with output 880, while the other similar demodulator circuits are numbered 1010, 1012, 1014, 1016, and 1018, respectively for geometric angles of 150, 210, 270, 330 (or −30), and 30 degrees. For briefer identification, these coils are number sequenced 1 through 6 (as labeled on the demodulator boxes) starting from the 90-degree coil and proceeding counterclockwise as in the previous sentence, ending at 30 degrees. The vertical position signal "Zs" from amp 1052 is an equal-weighting sum of the outputs of all six demodulators. Differences of opposite demodulator outputs are taken, reducing the six signals to three 120-degree axis differentials: the difference of demodulator outputs 2 minus 5 at amp 1050 (labeled "2–5" on the op amp, and similarly for the next two), outputs 3 minus 6 at amp 1048, and outputs 4 minus 1 at amp 1046, corresponding to detection axes at angles −30 degrees, +30 degrees, and +90 degrees. These three outputs are summed into two amplifiers, 1054 giving x-sense and y-sense angles Θxs and Θys. When a vector is resolved into an X-axis component, the weighting factor is the cosine of the angle, while resolution of a Y-axis component involves the sine of the angle. The x-sense weighting factors, as labeled on the wires connecting into 1054, are the cosines of the three angles just given, +0.866, +0.866, and 0.000 (to three place approximation), with the zero-weight-factor connection to amp 1054 being omitted. The y-sense weight factors are the sines of the same three angles, namely −0.500, +0.500, and +1.00, as labeled on the three inputs to amp 1056. The three sense signals, Zs, Θxs, and Θys, from amps 1052, 1054, and 1056, are compared with externally-provided target voltages Zt, Θxt, and Θyt, on wires 1094, 1092, and 1093, the differences being operated upon by PID circuits 900 (labeled after the example of FIGS. 9a and 9b), 1060, and 1058. The resulting drive outputs are labeled Zd, Θxd, and Θyd on wires 1082, 1080, and 1078. The "Zd" signal on 1082 feeds into the six coil drive amplifiers 1034, 1036, 1038, 1040, 1042, and 1044 with equal weightings, where these drive amplifiers respectively drive the circuits associated with demodulators 2, 3, 4, 5, 6, and 1, associated with angles of 150, 210, 270, 330 (or −30), 30, and 90 degrees. These same six driver amplifiers receive weighted sums of x-tilt and y-tilt drive data. Three amplifiers intermediate between the PID drive outputs and the six coil drive amps (as just listed) are shown with inputs labeled by the angle sines and cosines, the same factors associated with amps 1054 and 1056. Of these three, amp 1062 is associated with the angle −30 degrees. Its input from the x-tilt drive 1080 is weighted +0.866, the cosine of −30 degrees, while its input from the y-tilt drive 1078 is −0.500, the cosine of −30 degrees. Similarly, amp 1064 is associated with the angle +30 degrees, with its x-tilt and y-tilt weighting factors being +0.866 and +0.500, the cosine and sine of +30 degrees. Amp 1066 gives a weighting factor of +1.00 to its single non-zero input, the y-tilt drive 1078, this weighting being the sine of 90 degrees, with the cosine being zero. From the outputs of these three amps, the output of 1062, associated with −30 degrees, goes to amp 1034 with a positive weighting, and thence to 150-degree coil circuit 1010, and on the opposite side to amp 1040 with an equal negative weighting, and thence to 330 (or −30) degree coil circuit 1016. Similarly the output of 1064, associated with +30 degrees, goes to amp 1036 with positive weighting and amp 1042 with equal negative weighting, driving the angles 210 and 30. Finally the output of 1066, associated with +90 degrees, goes to amp 1038 with positive weighting and amp 1044 with equal negative weighting, driving the angles 270 and 90. Thus, the six amps with even numbers 1034 through 1044 each receive two inputs, one of which is always the same weighting and associated with the z-axis drive, while the other inputs are weighted +,+,+,−,−,−, giving + and − pairs of weightings for diametrically opposite coils. In sequence, these six amps are associated with the detector/demodulator circuits 1010, 1012, 1014, 1016, 1018, and 800, closing the servo control loop where we began with the diagrammatic hexagon of coils and demodulator circuits. Note that unity buffer amp 1066 is shown for artistic symmetry with amps 1062 and 1064, illustrating the threefold symmetry of the 120-degree axes of the pairs of coils. Conceptually, this buffer could have been drawn as a wire. Similarly, the separate op amps used to illustrate weighting by sines and cosines and then weightings by equal magnitudes of + and − gains could have been combined into fewer op amps, each with more summing inputs—as was done in practice for hardware implementation of this invention. FIGS. 10a and 10b are for conceptualization. Note that the polarity of feedback, degenerative or regenerative, might be off for any of the three control types, tilt, or z-axis translation (FIG. 10a), or (x,y)-axis translation (FIG. 10b), depending on the phase of beacon signal 1030 relative to the demodulator reference phase 1032, and depending on consistency of the polarity conventions among the various figures. The polarity conventions of FIG. 5c provide an unambiguous winding polarity convention, but polarity for each of the three types of servo loop must be checked.

FIG. 10b circuitry shares in common the beacon 422 (as driven from 1030) and the phase reference 1032 from FIG. 10a, where the variable magnetic couplings from the beacon and the fixed wiring from the phase reference to the individual demodulators is not shown explicitly in FIGS. 10a and 10b, nor in FIGS. 8a and 8b. Translation drive coil assembly 750 is shown on a smaller scale than in FIG. 7b, and the detailed labeling of FIG. 7b, correlating with the physical positions illustrated in FIG. 6, is not repeated. The sequence of angles of coil action is different in this translation-drive diagram than for the tilt drive diagram of FIG. 10a. Detector/demodulator circuit 1020, with sequence number 7 of the 9 demodulators, is associated with an angle of +210 degrees, going from the positive or counterclockwise rotation sense of the coil at +210 degrees (labeled 630 in FIG. 7b) to the negative or clockwise rotation sense of the coil pair at +30 degrees (labeled 624 and 636 in FIG. 7b). Similarly, circuit 1022, with demodulator sequence number 8, is associated with +330 or −30 degrees and coil 632, opposed with the opposite-rotation paired coils 622 and 634 at 150 degrees. Circuit 1024, with demodulator sequence number 9, is associated with +90 degrees and coil 628, opposed with the opposite-rotation paired coils 626 and 638 at +270 degrees. Hence, the angles associated with the demodulators are spaced by 120 degrees in FIG. 10b, as opposed to 60 degrees in FIG. 10a. Amp 1084, with output "Xs" for sensing of X position, has as its input weightings the cosines of the angles given above: −0.866 for circuit 1020, demodulator 7, and +210 degrees; +0.866 for circuit 1022, demodulator 8, and +330 or −30 degrees; and zero weighting, or no input, for circuit 1024, demodulator 9, and the cosine of 90 degrees. Amp 1086, with output "Ys" for sensing of Y position, has as its input weightings the sines of the same angles just given, from the same three circuit numbers and demodulators. The "Xs" sense signal from 1084 is paired with the "Xt" target signal from an external source, coming into PID circuit 1070 on wire 1096. The "Ys" sense signal from 1086 is similarly paired with the "Yt" target signal from an external source, coming into PID circuit 1068 on wire 1098. The PID outputs from 1070 and 1068 are respectively labeled "Xd" and "Yd", for the X and Y drive signals, identified with wires 1090 and 1088. These two signals go into three weighted summing amplifiers, 1072, 1074, and 1076, analogous to 1062, 1064, and 1066 of FIG. 10a except for the differences in the angles taken. The "Xd" signal on 1090 goes into summing amp 1072, with a weight of −0.866, the cosine of the +210 degrees associated with 1072's output and circuit 1020, sequence number 7. Similarly, "Xd" to summing amp 1074 is weighted +0.866, the cosine of +330 or −30 degrees associated with 1074's output and circuit 1022, sequence number 8. "Xd" does not have a summing connection to amp 1076, whose output is associated with circuit 1024, sequence number 9, and +90 degrees, whose cosine is zero. For "Yd" on 1088, the associated sequence of detector/demodulator circuits, demodulator sequence numbers, and angles, are the same as just described, except that the coefficient is the sine of the angle: −0.500, −0.500, and +1.00 for the weights to 1072, 1074, and 1076. This completes the description of the position control loop.

A Simplified Servo

Figure 10C:
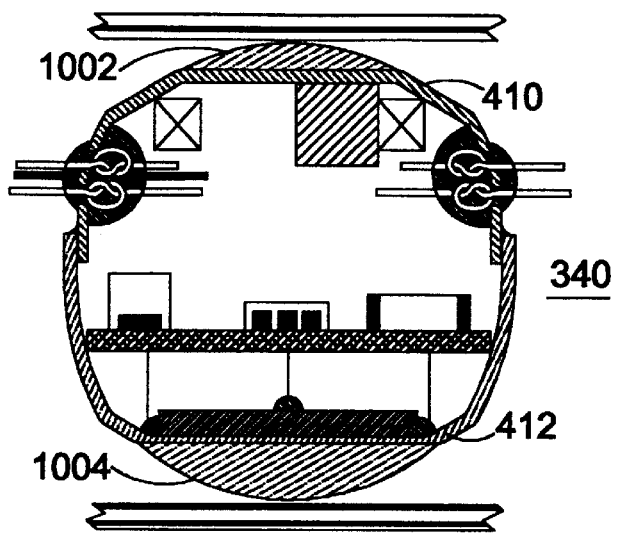
FIG. 10c shows a view similar to FIG. 4b, but with the top and bottom surfaces of the rotor modified to a spherical shape, so that vertical motion of the rotor can be restricted mechanically without need for a vertical channel of servo control.

Control of axial position is fairly costly in terms of drivers and demodulators, as is seen by comparing FIGS. 10a and 10b. Although the circuitry of FIG. 10b drives nine coils, the coils are interconnected so that only three drive circuits and three demodulator circuits are required. The circuitry of FIG. 10a drives just six coils, but each coil requires a separate driver and demodulator. The extra circuitry is needed to handle the "common mode" information that drives and measures position in Z, while "differential mode" signals between opposing pairs of coils are used to sense and drive tilt in X and Y. For the smoothest, tightest possible control of levitation, servo control of Z is needed. If Z-axis position is not controlled, however, the rotor cannot travel very far off center in Z before encountering a confining surface. Consider a simplified and more economical design in which position in Z is not controlled electronically, while uncertainty of Z-axis position is minimized by changing the shape of the rotor. As originally drawn in FIG. 3 and subsequently, the front surface of rotor 340 was made flat, since the ultrasound transducer 424 communicating through that surface is flat. One can, however, bond to the flat front surface of 340 a lens-shaped piece of plastic. As shown in the elevation section view of rotor 340 in FIG. 10c, polymer lens 1004 is bonded to 412, the rotor half-shell for the ultrasound transducer side. 1004 is flat on the surface that bonds next to the ultrasound crystal face and is spherical on the surface facing outward to the ultrasound fluid. There are materials, e.g. certain formulations of polyurethane rubber elastomer, that approximate water in density and in sound transmission speed, such that their addition to the surface of an ultrasound rotor makes little difference either to buoyancy or to ultrasound focusing. Other materials with a positive ultrasound refractive index relative to water will give convergent focusing of the ultrasound beam, which would be desirable in some designs. The choice of material for 1004 controls the degree of ultrasound beam focusing, if any. A second lens, 1002, is bonded to 410, the rotor half-shell containing the magnets and beacon coil. Like lens 1004, the flat side of lens 1002 is bonded to the flat base surface upon which rest the permanent magnets 418, 419, and 420 (as labeled in FIG. 4a). The convex outer surface of lens 1002 is spherical about the same center point as the outer surface of lens 1004. Unlike lens 1004, lens 1002 has no ultrasound function, but simply modifies an outer contour of 340. This rotor ball is confined between parallel surfaces, as illustrated in FIG. 10c, where these surfaces could, e.g., be surface 543 adjacent to 1002 and ultrasound window surface 541 adjacent to 1004, where surfaces 543 and 541 are shown in FIG. 5b. With a small clearance between these parallel surfaces and the spherical surfaces of 1002 and 1004, the rotor ball 340 will be confined to rotate about a center whose Z-axis position can vary only slightly. As drawn, the rotor surfaces transition from spherical to conical where the outer edges of 1002 and 1004 are adjacent to the innermost parts of the conical portions of half-shells 410 and 412. These conical surfaces go outside the sphere defined by 1002 and 1004 and run into the confining surfaces (e.g. 543 and 541) defining the top and bottom of the rotor cavity when the tilt angle of rotor 340 reaches a predefined upper limit, e.g., 35 degrees off axis. Thus, as in the previous design, rotor 340 is prevented from flipping upside down. With little latitude for uncontrolled movement in Z, the uncertainty of Z-axis position will be very small even if there is no servo control in Z. Furthermore, with a neutrally buoyed rotor, there will be little bumping and frictional interference with the confining surfaces. With the rotor thus modified to just fit the plenum in which it travels, the circuitry for control of the tilt coils can be simplified, as is now explained.

Figure 10D:
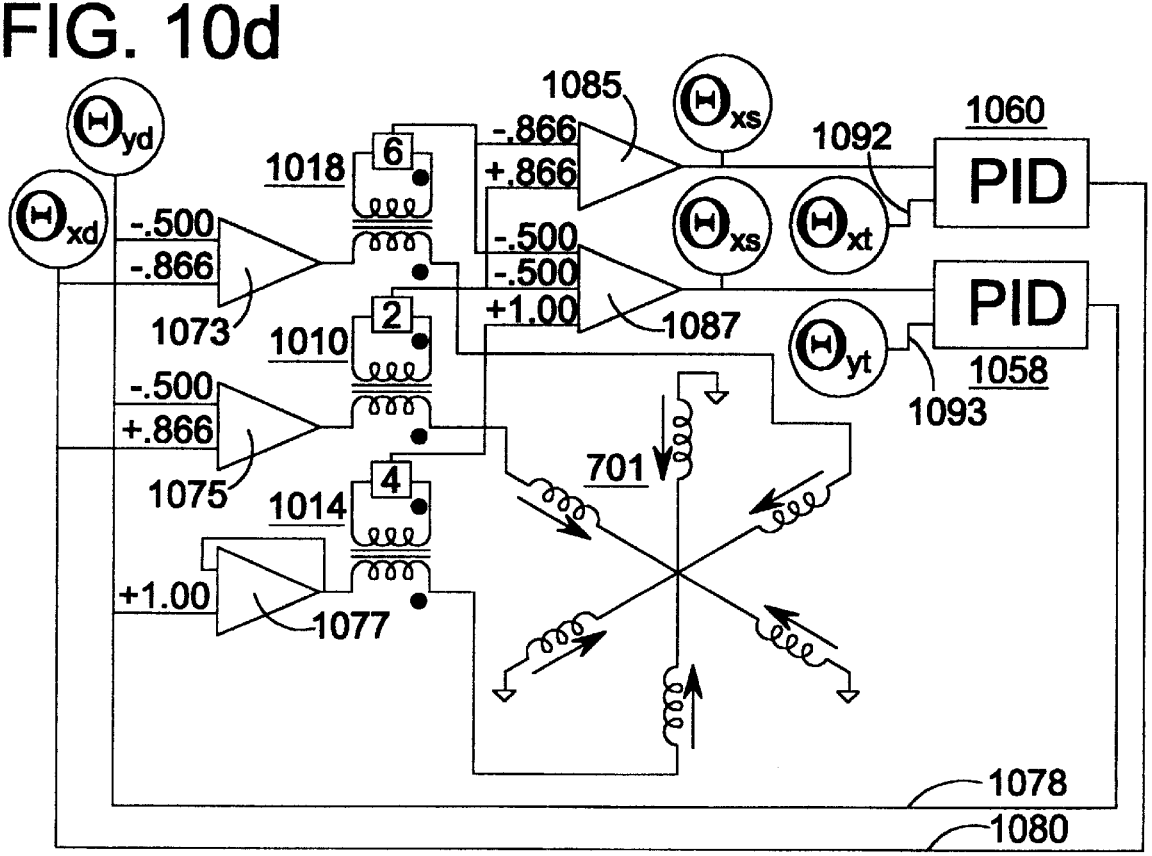
FIG. 10d shows how circuitry of FIG. 10a can be simplified by the elimination of the vertical channel of servo control, as permitted, e.g., by the geometric modifications of FIG. 10c.

FIG. 10d shows a simplified variation of the circuitry of FIG. 10a, where there is no control of Z-axis position. Upon comparison to the circuitry of FIG. 10b, it is seen that the topology of the FIG. 10d schematic is identical except for the substitution of coil assembly 701 in 10d for coil assembly 750 in 10b. 701 is like coil assembly 700 of FIG. 10a (and first shown in FIG. 7a) except that the common ground 650 at the middle of the collection of coils in FIG. 7a has been eliminated. In 701, three wires cross straight across the center of the coil group without connection, one wire on a vertical axis, one wire at an angle of +30 degrees with respect to a horizontal to the right, and the remaining wire at −30 degrees with respect to the same horizontal. Thus, in the order of these angles and referring to the coil labels of FIG. 7a, coil 610 is connected to coil 620, coil 618 is connected to coil 614, and coil 612 is connected to coil 616. These three series pairs of coils are driven from one end and grounded at the opposite end. The series connection causes each pair of coils to contribute in the same direction to a horizontal magnetic field across the center of the rotor cavity, in the so-called differential mode of operation. This is in contrast to the common mode of operation where all six coils are excited in the direction of the arrows associated with the coils, or all in the opposite direction, so that the field vectors all point toward or all point away from the center. This common mode of operation is eliminated in FIG. 10d. Driver summing amplifiers 1072, 1074, and 1076 of FIG. 10b become amplifiers 1073, 1075, and 1077 in the analogous diagram of FIG. 10d. These drivers respectively couple to transformer and demodulator assemblies 1018, 1010, and 1014, which are equivalent to the assemblies numbered the same in FIG. 10a. The transformer and demodulator assemblies opposite these three in FIG. 10a, namely 1012, 1016, and 800, are eliminated by the series connection of the three pairs of coils, as are the three driver summing amplifiers formerly feeding into these assemblies. Associated with 1018, 1010, and 1014 are demodulator sequence numbers 6, 2, and 4, marked on the demodulator boxes and corresponding to the sequence numbers of FIG. 10a. By analogy to circuits 1020, 1022, and 1024 plus demodulators of sequence numbers 7, 8, and 9 of FIG. 10b, circuits 1018, 1010, and 1014 and the associated demodulator sequence numbers 6, 2, and 4 drive series-connected coil sets associated with driven coil pairs at angles of +210, +330 (or −30), and +90 degrees, while the demodulator outputs drive summing amplifiers 1085 and 1087 analogous to summing amplifiers 1084 and 1086 of FIG. 10b. All of summing amplifiers 1073, 1075, 1077, 1085, and 1087 have the same input angle cosine weightings as the analogous amplifiers with numbers one unit lower (e.g., 1072 analogous to 1073, etc.) The outputs of amplifiers 1085 and 1087 drive PID circuits 1060 and 1058, the equivalents of the circuits by the same numbers in FIG. 10a and sharing the same target inputs, 1092 and 1093, and the same output wires, 1080 and 1078, in both FIGS. 10a and 10d. The labeling for X and Y angular drive, sense, and target signals is the same for FIGS. 10a and 10d. Components 1026, 1028, 1030, and 1032 of FIG. 10a are retained in the modified topology, serving the same functions as before, though they are not redrawn in FIG. 10d. All of the circuitry associated with servo control of translation in Z goes away in the modifications going from FIGS. 10a to 10d.

While the tilt circuit topology of FIG. 10d is seen to be like the translation circuit topology of FIG. 10b, the loop gains and time constants, set in the PID circuit coefficients, will not in general be the same for the two types of circuits. This is because tilt drive circuits and coils do not behave dynamically like translation drive circuits and coils.

Dynamic Adjustments

As just indicated above, in tuning a multi-axis servo system of the type described here, the gains for the servo loops in various channels will differ unless special adjustments are made. A definition of servo loop gain starts with the ratio of acceleration in a sensed feedback signal to an associated drive voltage. This ratio is modified, as a function of frequency, by the PID transfer function, leading to the total frequency-dependent loop gain. Loop gain is affected by coil resistance, by magnetic force-per-ampere or torque-per-ampere of coil current affecting the rotor, by translational or rotational inertia, and by the gain factor relating translation or rotation to the sensed feedback signal. The electromagnetic interactions giving rise to tilt are quite different than those giving rise to translation, i.e. field strength versus field gradient. Tilting fields and forcing gradients are generated by very dissimilar coils. Where it is used, translation in Z is driven quite differently from translation in X and Y, using different coils. For inertias subjected to the forces of translation and rotation, one compares masses for translation with mass moments of inertia for rotation. Mass of displaced water also enters the equation for effective inertia in different modalities. For a neutrally buoyed sphere undergoing small transient motions (and therefore not developing the turbulent wake associated with steady motion), the effective total translational inertia is 1.5 times the mass of the sphere itself, with the additional 50% associated with mass of entrained moving liquid. For rotation, the mass addition is small and associated with the minor irregularities by which the rotor departs from a spherical shape. It is not hard to see that there are three different gain characteristics associated with the three types of loops, for (x,y)-tilt, (x,y)-translation, and z-translation. For optimum performance, therefore, the gains and time constants of the PID loops need to be tuned somewhat differently for the three types of control loops.

Adding more control sophistication for enhanced performance, the servo loops can include cross-couplings to compensate for known characteristics of the driven system. In particular, the design of the preferred embodiment described here places the beacon coil and magnet at one end of the ultrasound rotor, significantly away from the center of gravity. Because of this offset, a translational magnetic force exerted on the magnet carries a torsional component relative to the center of gravity of the rotor. Similarly, rotation affects translation because of the same offset between the mass center and the magnet center. The tether cable or cables are ideally attached in the plane of the rotor magnet, in order to avoid a torsion-producing radius between magnet force and tether force. If the operator attempts to jerk the ultrasound rotor to a new position, the rotor will tilt one way as it accelerates and the other way as it decelerates. It is apparent that a translation drive that combines linear force with a compensatory tilting torque can reduce the unwanted cross coupling between translation and rotation. Ignoring tether torsional moments (which are minimized by tether attachment in the plane of the rotor magnet), this compensatory torque signal should go through a highpass filter, reducing the compensation to zero at a rate consistent with the transition from inertia-limiting to tether-force-limiting of travel. A similar compensation couples rotation to translation. It is also desirable to have the system response time fairly well matched between translation and rotation, so that the system will "catch up" to abrupt operator input changes by a comparatively straight path in the space of the controlled degrees of freedom. Looping dynamic paths in 5-space are not desirable.

An Almost Unidirectional Computer Interface

The embodiment just described is an analog feedback system designed to make the ultrasound rotor track five target inputs in its five degrees of freedom of translation and rotation (or four target inputs in four degrees of freedom for the simplified version of FIG. 10d). The five targets are readily provided by digital/analog outputs from a computer interface. The system operator normally controls four degrees of freedom, while position in Z is automatically maintained on or near the equatorial symmetry plane of the coils, either by servo control or by confining mechanical boundaries. Because of symmetry, the Z=0 plane in beacon coordinates is flat, so that it is advantageous to design the rotor enclosure with centering defined by beacon coil travel in this plane (since beacon coil position is controlled, while the magnetic center may be slightly above or below the beacon coil center without significantly degrading servo performance.) A four axis joystick has been used for setting the control position, based on a beacon coil at the end of a hand-controlled stick and moved in a set of coils of identical or geometrically similar (i.e. identical except for a linear scale factor) to those that drive and sense rotor motion. The operator moves and tilts this joystick with the same motions that would be used to move and tilt a hand-held ultrasound transducer over the skin surface of a patient. A more economical approach, however, is use of a computer mouse. In a preferred embodiment, mouse motion with the primary button depressed (i.e. the left button for a right-handed mouse) controls translation at near-constant tilt, while mouse motion with the primary button released controls tilt. In the tilt mode, translation and tilt are readily coordinated such that the pivot point of the ultrasound beam, the point of null translation, lies at the expected level of an ultrasound window in the skull. By this means, once an ultrasound window is located, the operator can readily explore the angular space looking into the cerebral vasculature without concern for maintaining beam positioning to pass through the window. Note that a matching of response times for translation and rotation will help maintain the ultrasound beam aligned through a window during transient accelerations and decelerations.

If the ultrasound rotor is not visible to the operator (as is frequently the case in practical applications), then a schematic screen representation of rotor position and alignment can aid coordination. A further feature to add is perspective or two-view representation of the location, within the skull, of the sample volume from which an ultrasound echo is obtained. From this capability, another step brings about screen memory and cumulative mapping of incoming flow data, painting a Doppler flow image as if with a paintbrush.

In practice, the operator will cause the ultrasound rotor to bump into mechanical limits of translation and rotation. As mentioned earlier, transformer intermodulation distortion can cause latchup problems near a boundary. Even when intermodulation distortion is reduced to a negligible level, overload of the integrators in the feedback loop can cause hanging on a boundary. If analog/digital conversion from analog channels back toward the control computer is performed, sustained overload due to boundary contact (as opposed to transient overload when acceleration limits are reached) can be detected. It is useful, when detecting an overload, to provide visual display indicative of the boundary encounter. Simultaneously, zeroing of the affected analog integrators like the one built around amp 960 (FIG. 9a) will quickly unhang the rotor. If the target position in 5-space remains beyond a boundary and integration is resumed immediately after reset, the rotor will again bump the boundary, setting up a bumping oscillation. Normal control cannot be maintained when a boundary prevents access to a needed rotor location. An appropriate software solution entails advising the operator to back off from the confining boundary and, if necessary, relocate the control head on the patient in order to make the desired rotor position and alignment mechanically accessible.

Although the control space mapping by beacon coordinates has reasonable linearity with respect to Cartesian (x,y,z) coordinates and directional tilt cosines in x and y, small mapping corrections may readily be performed in the digital domain, in applications where the added accuracy is needed. Because the control loop is almost linear in its various channels, however, the servo control loops can be closed in linear fashion, yielding reasonably consistent settling response throughout the control range. In applications requiring accurate absolute geometric knowledge of rotor position and orientation, nonlinear digital mapping corrections may be applied to the target signals that the servo loop is asked to track, rather than inside the control feedback loop. As long as the analog servo controller normally settles accurately to the target input vector, then the only need for information flow from the controller back to the computer is for detection of overload conditions where boundaries are encountered—as indicated when position errors are not reduced nearly to zero over time. Boundary detection can cause the digital computer controller, first, to reset the PID integrators, and second, to bring the target output vector back within the boundaries geometrically accessible to the servo system. Keeping digital linearity corrections out of the servo loop substantially simplifies the design, eliminating the need for real-time bidirectional data transfer and the timing problems of real-time dynamic control.

Description of Digital Control With Beacon Coil as Receiver

The boundaries between the analog and digital parts of the servomechanism in the current system can obviously be moved. In a five-axis controller, one can have analog/digital conversion occur immediately after synchronous detection and filtering, in nine channels rather than five matrixed channels. One can similarly have digital/analog conversion occur at the nine coil-drive channels. In this case, the matrixing and PID functions are incorporated in the digital domain, bringing the entire control loop under software control. The designer of such a system then has to deal with real time dynamic control but gains tremendous advantages of design flexibility for making subtle adjustments of the servo system.

Digital sampling before synchronous demodulation, with demodulation taking place in software, is obviously conceivable, though demanding of speed in data acquisition and processing. Such a system permits other simplifications, however, making the approach worthwhile in certain contexts, as will now be shown.

Figure 11:
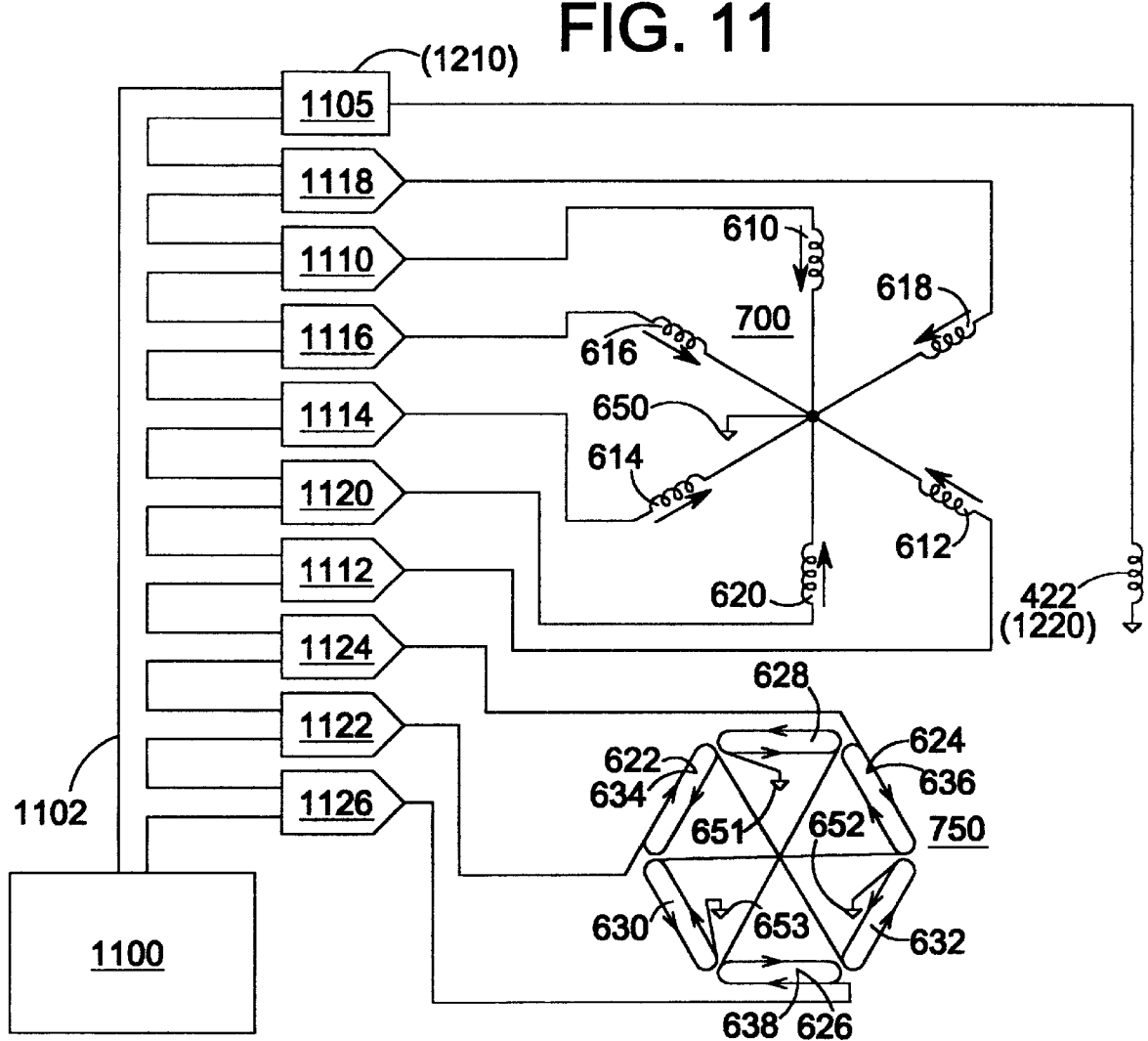
FIG. 11 illustrates the use of a beacon coil as a detector of high-frequency signals superimposed on the drive signals to multiple stator coils, where the separation of signals received by the beacon coil according to drive coil origin is accomplished by multiplexing in frequency or time.

An alternative embodiment of the servo control electronics is illustrated in FIG. 11, taking advantage of multiplexing and digital domain operation to accomplish a substantial reduction in hardware. This approach puts out electromagnetic energy at more frequencies than the embodiment previously described, which may or may not make an important difference, depending on the context of operation.

As shown schematically in FIG. 11, each of the nine driven coil circuits of earlier figures is driven by a separate digital/analog converter, or DAC, with an amplifier output stage of appropriate drive capacity. These converters are labeled 1118, 1110, 1116, 1114, 1120, 1112, 1124, 1122, and 1126, respectively driving the coils 618, 610, 616, 614, 620, 612, 624, 622, and 626. These coil numbers in the 600s refer back to the original pictorial appearance of these coils in FIG. 6, though they appear diagrammatically in radial-axis coil assembly 700 and axial coil assembly 750, appearing originally in FIG. 7b and again in later figures, including here in FIG. 11. Beacon coil 422, physically the same coil as appeared originally in FIG. 4a, is used as a receiver rather than a transmitter, being connected to receiver module 1105. This module includes an analog/digital converter or ADC and may also include analog signal conditioning and pre-processing hardware prior to analog/digital conversion. All the digital/analog converters, or DACs, mentioned in this paragraph, plus analog/digital converter, or ADC, 1105, share digital bus 1102 for communication with a digital controller 1100. For 1100, any of a number of devices could be used, including a general purpose microprocessor with sufficient speed, or a digital signal processor (DSP) chip adapted to high-speed signal processing. Many detailed modes of operation are possible within the general framework that the DACs generate low-frequency coil drive signals and superimposed high-frequency beacon signals, while the receiver module receives all the information, which needs to be sorted out by channel and by the signed amplitude (i.e. representing a positive or a negative coupling) of each channel. Among the many approaches to sorting out channel data, three broad categories are readily identified: frequency domain multiplexing, time domain multiplexing, and hybrids of frequency and time domain multiplexing.

One hybrid method worth mention is wavelet encoding, where the waveform going out on each channel is a complex waveform burst emerging over the interval of several data samples in sequence. Each channel puts out a different burst shape at the same time. The wavelet encoding method produces pulse shapes that are readily separated at the decoding end of the process, after arriving lumped together in a single receiver channel. Each member in an orthogonal family of wavelet shapes is analogous to a separate frequency band for frequency domain encoding/decoding. Unlike frequency methods, however, wavelet encoding is adapted to waveforms that are confined to discrete, limited time windows.

While wavelet encoding may prove to have advantages over other alternatives, a much simpler approach will be described for use with the embodiment of FIG. 11. By a straightforward time-domain multiplexing approach, a simple pulse is superimposed on the output of each DAC output in a cyclic sequence. To assure overhead for the pulse, the pulse on each channel is caused to go in the opposite direction from the ongoing low-frequency coil drive signal present when the pulse is to be applied. The pulse height can then be set at the half-scale DAC range, i.e. the distance from DAC center-scale to the most negative or most positive limit of the range. The pulse will start from a baseline of zero or, more usually, from the non-zero polarity baseline of the low-frequency coil drive signal, and go to the polarity opposite that of the baseline. With the DAC channels numbered in sequence from one to nine, e.g. using the numbers associated with the nine demodulator channels of FIGS. 10a and 10b, then a pulse goes out on channel one, a quiescent no-pulse period follows, then a pulse goes out on channel two, followed by another quiescent period, etc., in sequence through channel nine and looping back to channel one for another repetition. The signals received at 1105 are identified by time window with the associated drive channel. For decoding purposes, received signals are identified with the polarity of the output pulse, so that the receiving system "knows" whether the measured electromagnetic coupling is inverting or non-inverting. Each drive signal may be biased slightly in the opposite direction of the outgoing pulse on that channel so that, on average, the low-frequency content of each drive channel is unaltered by the pulses. Such biasing may become important as the drive channel output crosses zero and the polarity of the superimposed pulse train reverses. Compensation of the average level then minimizes crossover distortion and the potential for servo jitter at zero.

As mentioned earlier, eddy currents in the permanent magnet surrounded by beacon coil 422 absorb coil power when the coil is in a transmit mode. Subdivision of a metal magnet into smaller component magnets was previously described as a means to reduce signal power loss. When coil 422 serves as a receiving rather than transmitting antenna, the effects of eddy currents on transmission have direct implications for reception, including both gain and phase dispersion, because of the symmetry between the receiving and transmission properties of a passive antenna. Where eddy currents dissipate power from a continuous transmission carrier sinusoid, one can be assured that the eddy current interaction with the coil will attenuate received signals. Furthermore, the phase dispersion associated with the frequency dependence of eddy current interaction will cause some spreading over time of received pulse signals. Breaking up the permanent magnet in order to break up eddy currents can reduce the attenuation and phase dispersion of received signals. For a frequency band in the vicinity of 50 kHz, the subdivision of a single magnet into four component magnets is sufficient to bring eddy-current attenuation of received and transmitted signals below 6 db while bringing phase dispersion down to a relatively easily managed level. Some simple analog frequency and phase compensation in module 1105 can reduce the time-smear caused by eddy current interaction with the permanent magnet or magnet cluster, substantially reducing the digital processing required for adequate channel separation. The specific choices to be made will depend on the details of the application.

A Beacon with No Tether

An induced beacon signal was described in the prior art, for wireless transmission of energy to a beacon coil, such that a rotor could be levitated with no connecting cable. A freely levitating rotor can serve as a translating and rotating mirror for ultrasound signals, offering advantages for some applications. The general approach to an induced beacon is illustrated schematically in FIG. 12. 1210 is an excitation source, typically providing a continuous output of a high-frequency signal. This excitation is applied to a stator winding 1220, which may be a combination of drive windings or may be a separate small winding dedicated to energizing the induced beacon. 1220 is coupled inductively, via a mutual inductance indicated by double-arrow 1230, with beacon coil 422, which in turn is connected with a load 1200. The only load described in the prior art was a short circuit. As described in the prior art, the shorted beacon winding or single loop perturbs the inducing field of 1220, and the geometric pattern of the perturbation is detected in the various drive coils. A problem with this approach is that any conductor or ferromagnetic substance brought near the system and coil 1220 will perturb the field of 1220, causing a response that is not distinguishable, or not readily distinguishable, from the variable position-dependent influence of coil 422. When all the beacon coil energy originates directly from 422, via direct wiring of the coil, then the sensitivity to external influence is much smaller. This goal of reduced sensitivity to interference can be accomplished in ways not anticipated in the prior art.

To make the signal induced in coil 422 readily distinguishable from the excitation signal coming from 1220, it is possible to design a module 1200 that generates frequency content not present in the output from 1210 as transmitted by 1220. Two simple examples are given. Module 1200 can consist of simple semiconductor diode 1240, which causes current flowing through 422 to flow in unipolar pulses. The resulting pulse train will contain distortion harmonics of the frequency from 1210 via 1220, including a strong second harmonic distortion. A selected distortion harmonic may be used as the carrier frequency of the system, while the excitation frequency from 1210 is rejected in the decoding process. In an alternative embodiment, module 1200 consists of oppositely-directed parallel semiconductor diodes 1250 and 1260. (Schottky barrier diodes can also be used for 1240, 1250, and 1260.) The forward bias threshold on these diodes is used to generate a crossover distortion of the excitation signal from 1210 via 1220. With matched diodes and an appropriate voltage level induced in the beacon coil (as determined by excitation field strength and number of windings in the beacon coil), the crossover distortion will contain a strong third harmonic content, which can be used as the carrier frequency of the system. This latter approach has the advantage that, with the forward diode voltage being comparatively insensitive to current level, the strength of the emitted third harmonic signal will depend on this insensitive forward voltage level and will be comparatively insensitive to variations in the excitation level originally induced in the beacon coil, as the coil moves and rotates.

Figure 12:
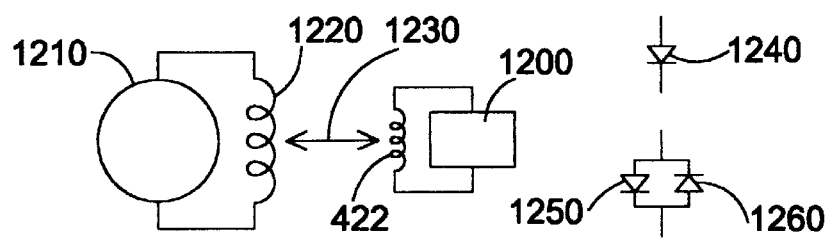
FIG. 12 illustrates a beacon coil excited by an excitatory field from a fixed coil and transforming part of the received excitation energy into another frequency for beacon carrier detection, the new frequency being generated, e.g., by one diode or two diodes in parallel.

A final configuration for the system is described by a combination of FIG. 11 and FIG. 12. In FIG. 11, beacon coil 422 is labeled with a second number directly below in parentheses: (1220). Similarly, receiver module 1105 is labeled with a second number in parentheses: (1210). By these alternate designations, 1220 in FIG. 11 represents a fixed coil, dedicated to reception of output from the beacon coil, where the beacon coil itself is not shown in this interpretation of FIG. 11. Pulses from the drive coils excite responses in beacon coil 422, which is equipped with distortion-producing components in 1200, e.g. diode 1240 or diode pair 1250 and 1260, resulting in magnetic field patterns in time and space that are distinguishably different from the field patterns coming from the drive coils. The distortion output of 422 is received by 1220, by way of the mutual inductance indicated by double arrow 1230 of FIG. 12, and this distortion signal is received, amplified, and possibly partially decoded or pre-processed by hardware in 1210. The output of 1210 is converted to a digital signal which goes via bus 1102 to digital controller 1100 for completion of the decoding process. By this approach there is no tether connection for the beacon coil, the beacon is excited sequentially by drive coils, and the resulting signal is received in a single dedicated hardware channel, whose function need not combine driving and sensing. Accompanying the hardware simplification is an inevitably more involved process of sorting out and interpreting received signals. Variable responses in the system include variable couplings from drive windings to the beacon coil, which are to be quantified, plus additional variability in efficiency of distortion generation and variable coupling of distortion information from the beacon coil back to the fixed antenna coil 1220. The added sources of variability complicate the signal processing needed to infer rotor position, which is the tradeoff for obtaining substantial hardware reductions.

Although the present invention has been described with particular reference to detailed designs, it is to be understood that all modifications and equivalents reasonably considered by those skilled in the art are deemed to be contemplated by the present invention as described in the following claims.

What is claimed is:

1. A levitation system to generate relatively linear and relatively orthogonal electromagnetic control couplings, said system comprising:

a) a stator;

b) a rotor, levitated within said stator and including a permanent magnet and a beacon coil aligned and concentric with said magnet;

c) a first means associated with said stator for controllably varying, in two orthogonal lateral dimensions, lateral gradients of a first magnetic field strength directed in an axial dimension; and, d) a second means associated with said stator for controllably varying in said two orthogonal lateral dimensions, a lateral magnetic field.

2. The system of claim 1 with said second means further comprising means for controllably varying in said axial dimension an axial gradient of a second magnetic field strength directed in said axial dimension.

3. The system of claim 2, wherein:

a) said rotor moves in said two orthogonal lateral dimensions in response to said lateral gradients;

b) said rotor tilts in said two orthogonal lateral dimensions in response to said lateral magnetic field; and, c) said rotor moves in said axial dimension in response to said axial gradient.

4. The system of claim 3 wherein said first means is a first overlapping set of windings in said stator and said second means is a second overlapping set of windings in said stator.

5. The system of claim 4 further comprising high frequency beacon coordinate detection means, for measuring the variable mutual inductances coupling between said beacon coil and sets of windings from said first and said second overlapping sets of windings.

6. The system of claim 5 further comprising:

a) variable targeting means, for generating error difference signals between variable target input signals and outputs from said beacon coordinate detection means;

b) drive means, for controllably varying said lateral gradients and said lateral magnetic field and said axial gradient; and, c) coupling means, from said variable targeting means to said drive means, for causing said error difference signals to be reduced dynamically in time.

7. The system of claim 3, further including ultrasound beam generation means, wherein said beam is controllably moved in said two orthogonal lateral dimensions and controllably tilted in said two orthogonal lateral dimensions, responsive to motions in said levitated rotor.

8. The system of claim 7, wherein said levitated rotor is connected to said stator by a balanced pair of tether cables.

9. The system of claim 5, wherein said permanent magnet is subdivided into two or more component pieces contributing to a single dipole field, where division into said two or more component pieces reduces eddy currents associated with the operation of said beacon coil.

10. The system of claim 5, wherein:

a) an external high-frequency electromagnetic field provides energy to said beacon coil;

b) nonlinear components associated with said beacon coil cause distortion components of the current waveform induced in said beacon coil by said high-frequency electromagnetic field; and, c) the electromagnetic field from said beacon coil associated with said distortion components is detected as part of said measuring of variable mutual inductances.

11. The system of claim 5, wherein high-frequency waveforms applied to said first and said second overlapping sets of windings in said stator induce currents in said beacon coil.

12. The system of claim 4, wherein said first overlapping set of windings includes three layers of windings, axially stacked, with the middle of said three layers rotated in relation to the top and bottom of said three layers by approximately half the angle subtended by a single winding within said three layers.

13. The system of claim 12, wherein each of said three layers contains three windings, and wherein, within each layer of said three layers, said three windings occupy angular sectors to divide a circle into substantially equal thirds.

14. The system of claim 12, wherein a property of said middle of said three layers is unlike properties of said top and said bottom layers, wherein said property of said middle of said three layers may be adjusted to provide more linear lateral gradients of said first magnetic field strength directed in said axial dimension than would be obtained with said middle layer being like said top and said bottom layers.

15. The system of claim 4, wherein said second overlapping set of windings includes two layers of windings, radially stacked, with the outer of said two layers rotated in relation to the inner of said two layers by approximately half the angle subtended by a single winding within said two layers.

16. The system of claim 15, wherein each of said two layers contains three windings, and wherein, with each layer of said two layers, said three windings occupy angular sectors to divide a circle into substantially equal thirds.

17. The system of claim 7, wherein:

a) said rotor is surrounded by an ultrasound-transmitting fluid; and, b) the weight of said rotor is substantially neutrally buoyed by said fluid.

18. A five-axis levitation system utilizing overlapping coils to generate relatively linear and relatively orthogonal electromagnetic control couplings, said system comprising:

a) a stator;

b) a rotor, levitated within said stator and including a permanent magnet and a beacon coil aligned and concentric with said magnet;

c) a first overlapping set of windings in said stator, for controllably varying, in two orthogonal lateral dimensions, lateral gradients of a first magnetic field strength directed in an axial dimension; and, d) a second overlapping set of windings in said stator, for controllably varying two things: first, in said two orthogonal lateral dimensions, a lateral magnetic field; and second, in said axial dimension, an axial gradient of a second magnetic field strength directed in said axial dimension.

19. The system of claim 18, wherein:

a) said rotor moves in said two orthogonal lateral dimensions in response to said lateral gradients;

b) said rotor tilts in said two orthogonal lateral dimensions in response to said lateral magnetic field; and, c) said rotor moves in said axial dimension in response to said axial gradient.

20. The system of claim 19 further comprising high frequency beacon coordinate detection means, for measuring the variable mutual inductances coupling between said beacon coil and sets of windings.

* * * * *